US008680317B2

(12) United States Patent
Johnston et al.

(10) Patent No.: US 8,680,317 B2
(45) Date of Patent: *Mar. 25, 2014

(54) PROCESSES FOR MAKING ETHYL ACETATE FROM ACETIC ACID

(75) Inventors: Victor J. Johnston, Houston, TX (US); Laiyuan Chen, Houston, TX (US); Barbara F. Kimmich, Bernardsville, NJ (US); Josefina T. Chapman, Houston, TX (US); James H. Zink, League City, TX (US); Heiko Weiner, Pasadena, TX (US); John L. Potts, Angleton, TX (US); Radmila Jevtic, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 925 days.

This patent is subject to a terminal disclaimer.

(21) Appl. No.: 12/699,024

(22) Filed: Feb. 2, 2010

(65) Prior Publication Data

US 2010/0197959 A1 Aug. 5, 2010

Related U.S. Application Data

(63) Continuation-in-part of application No. 12/588,727, filed on Oct. 26, 2009, now Pat. No. 8,309,772, and a continuation-in-part of application No. 12/221,209, filed on Jul. 31, 2008, now Pat. No. 7,820,852, and a continuation-in-part of application No. 12/221,141, filed on Jul. 31, 2008, now Pat. No. 7,863,489.

(51) Int. Cl.
*C07C 67/08* (2006.01)

(52) U.S. Cl.
USPC .......................................................... 560/1

(58) Field of Classification Search
USPC .......................................................... 560/1
See application file for complete search history.

(56) References Cited

U.S. PATENT DOCUMENTS

| | | | |
|---|---|---|---|
| 2,021,698 A | 11/1935 | Perkins | |
| 2,105,540 A | 1/1938 | Lazier | |
| 2,607,807 A | 8/1952 | Ford | |
| 2,744,939 A | 5/1956 | Kennel | |
| 2,882,244 A | 4/1959 | Milton | |
| 3,130,007 A | 4/1964 | Breck | |
| 3,478,112 A | 11/1969 | Adam | |
| 3,702,886 A | 11/1972 | Argauer et al. | |
| 3,729,429 A | 4/1973 | Robson et al. | |
| 3,864,284 A | 2/1975 | Clippinger et al. | |
| 3,990,952 A | 11/1976 | Katzen et al. | |
| 4,065,512 A | 12/1977 | Cares | |
| 4,228,307 A | 10/1980 | Zimmerschied | |
| 4,270,015 A | 5/1981 | Knifton | |
| 4,275,228 A | 6/1981 | Gruffaz et al. | |
| 4,317,918 A | 3/1982 | Takano et al. | |
| 4,328,373 A | 5/1982 | Strojny | |
| 4,337,351 A | 6/1982 | Larkins, Jr. | |
| 4,374,265 A | 2/1983 | Larkins, Jr. | |
| 4,395,576 A | 7/1983 | Kwantes et al. | |
| 4,398,039 A | 8/1983 | Pesa et al. | |
| 4,399,305 A | 8/1983 | Schreck | |
| 4,421,939 A | 12/1983 | Kiff et al. | |
| 4,443,639 A | 4/1984 | Pesa et al. | |
| 4,465,854 A | 8/1984 | Pond et al. | |
| 4,471,136 A | 9/1984 | Larkins et al. | |
| 4,480,115 A | 10/1984 | McGinnis | |
| 4,517,391 A | 5/1985 | Schuster et al. | |
| 4,521,630 A | 6/1985 | Wattimena et al. | |
| 4,550,185 A | 10/1985 | Mabry et al. | |
| 4,581,473 A | 4/1986 | Polichnowski | |
| 4,613,700 A | 9/1986 | Maki et al. | |
| 4,620,050 A | 10/1986 | Cognion et al. | |
| 4,678,543 A | 7/1987 | Houben et al. | |
| 4,692,218 A | 9/1987 | Houben et al. | |
| 4,696,596 A | 9/1987 | Russell et al. | |
| 4,710,086 A | 12/1987 | Naaktgeboren et al. | |
| 4,777,303 A | 10/1988 | Kitson et al. | |
| 4,804,791 A | 2/1989 | Kitson et al. | |
| 4,826,795 A | 5/1989 | Kitson et al. | |
| 4,843,170 A | 6/1989 | Isshiki et al. | |
| 4,886,905 A | 12/1989 | Larkins, Jr. | |
| 4,902,823 A | 2/1990 | Wunder et al. | |
| 4,978,778 A | 12/1990 | Isshiki et al. | |
| 4,985,572 A | 1/1991 | Kitson et al. | |
| 4,990,655 A | 2/1991 | Kitson et al. | |
| 5,008,235 A | 4/1991 | Wegman et al. | |
| 5,061,671 A * | 10/1991 | Kitson et al. | ............ 502/185 |

(Continued)

FOREIGN PATENT DOCUMENTS

| | | |
|---|---|---|
| CN | 1230458 | 10/1999 |
| CN | 102228831 | 11/2011 |

(Continued)

OTHER PUBLICATIONS

Rachmady, Acetic Acid Reduction by $H_2$ on Bimetallic Pt—Fe Catalysts, Journal of Catalysis 209, 87-98 (Apr. 1, 2002), Elsevier Science (USA).

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Ordóñez et al., The role of metal and support sites on the hydrogenation of acetic acid on Ru-based catalysts, 21st NAM San Francisco, CA, Jun. 10, 2009.

Pestman et al., The formation of ketones and aldehydes from carboxylic acids, structure-activity relationship for two competitive reactions, Journal of Molecular Catalysis A: Chemical 103 Jun. 14, 1995, 175-180.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

(Continued)

*Primary Examiner* — Johann R Richter
*Assistant Examiner* — Kofi Adzamli

(57) ABSTRACT

A process for hydrogenating acetic acid to form of ethyl acetate and mixtures of ethyl acetate and ethanol. The hydrogenation is done in the presence of catalyst, preferably on a support that optionally includes a support modifier.

52 Claims, 3 Drawing Sheets

(56) References Cited

U.S. PATENT DOCUMENTS

| | | |
|---|---|---|
| 5,124,004 A | 6/1992 | Grethlein et al. |
| 5,137,861 A | 8/1992 | Shih et al. |
| 5,149,680 A * | 9/1992 | Kitson et al. .................. 502/185 |
| 5,155,084 A | 10/1992 | Horn et al. |
| 5,185,308 A | 2/1993 | Bartley et al. |
| 5,241,106 A | 8/1993 | Inoue et al. |
| 5,243,095 A | 9/1993 | Roberts et al. |
| 5,306,845 A | 4/1994 | Yokohama et al. |
| 5,350,504 A | 9/1994 | Dessau et al. |
| 5,426,246 A | 6/1995 | Nagahara et al. |
| 5,475,144 A | 12/1995 | Watson et al. |
| 5,476,827 A | 12/1995 | Ferrero et al. |
| RE35,377 E | 11/1996 | Steinberg et al. |
| 5,585,523 A | 12/1996 | Weiguny et al. |
| 5,691,267 A | 11/1997 | Nicolau et al. |
| 5,719,315 A | 2/1998 | Tustin et al. |
| 5,731,456 A | 3/1998 | Tustin et al. |
| 5,767,307 A | 6/1998 | Ramprasad et al. |
| 5,821,111 A | 10/1998 | Grady et al. |
| 5,849,657 A | 12/1998 | Rotgerink et al. |
| 5,861,530 A | 1/1999 | Atkins et al. |
| 5,945,570 A | 8/1999 | Arhancet et al. |
| 5,955,397 A | 9/1999 | Didillon et al. |
| 5,973,193 A | 10/1999 | Crane et al. |
| 5,977,010 A | 11/1999 | Roberts et al. |
| 5,995,397 A | 11/1999 | Kim |
| 6,040,474 A | 3/2000 | Jobson et al. |
| 6,049,008 A | 4/2000 | Roberts et al. |
| 6,093,845 A | 7/2000 | Van Acker et al. |
| 6,114,571 A | 9/2000 | Abel et al. |
| 6,121,498 A | 9/2000 | Tustin et al. |
| 6,232,352 B1 | 5/2001 | Vidalin et al. |
| 6,232,504 B1 | 5/2001 | Barteau et al. |
| 6,294,703 B1 | 9/2001 | Hara et al. |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,509,290 B1 | 1/2003 | Vaughn et al. |
| 6,559,333 B1 | 5/2003 | Brunelle et al. |
| 6,603,038 B1 | 8/2003 | Hagemeyer et al. |
| 6,632,330 B1 | 10/2003 | Colley et al. |
| 6,657,078 B2 | 12/2003 | Scates et al. |
| 6,670,490 B1 | 12/2003 | Campos et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,727,380 B2 | 4/2004 | Ellis et al. |
| 6,765,110 B2 | 7/2004 | Warner et al. |
| 6,768,021 B2 | 7/2004 | Horan et al. |
| 6,812,372 B2 | 11/2004 | Janssen et al. |
| 6,852,877 B1 | 2/2005 | Zeyss et al. |
| 6,903,045 B2 | 6/2005 | Zoeller et al. |
| 6,906,228 B2 | 6/2005 | Fischer et al. |
| 6,927,048 B2 | 8/2005 | Verser et al. |
| 7,074,603 B2 | 7/2006 | Verser et al. |
| 7,084,312 B1 | 8/2006 | Huber et al. |
| 7,297,236 B1 | 11/2007 | Vander Griend et al. |
| 7,351,559 B2 | 4/2008 | Verser et al. |
| 7,375,049 B2 | 5/2008 | Hayes et al. |
| 7,425,657 B1 | 9/2008 | Elliott et al. |
| 7,507,562 B2 | 3/2009 | Verser et al. |
| 7,518,014 B2 | 4/2009 | Kimmich et al. |
| 7,538,060 B2 | 5/2009 | Barnicki et al. |
| 7,553,397 B1 | 6/2009 | Colley et al. |
| 7,572,353 B1 | 8/2009 | Vander et al. |
| 7,608,744 B1 | 10/2009 | Johnston et al. |
| 7,884,253 B2 | 2/2011 | Stites et al. |
| 7,888,082 B2 | 2/2011 | Verser et al. |
| 7,994,368 B2 | 8/2011 | Johnston et al. |
| 8,071,821 B2 | 12/2011 | Johnston et al. |
| 8,309,772 B2 | 11/2012 | Weiner et al. |
| 2003/0013908 A1 | 1/2003 | Horan et al. |
| 2003/0077771 A1 | 4/2003 | Verser et al. |
| 2003/0104587 A1 | 6/2003 | Verser et al. |
| 2003/0114719 A1 | 6/2003 | Fischer et al. |
| 2003/0191020 A1 | 10/2003 | Bharadwaj et al. |
| 2004/0195084 A1 | 10/2004 | Hetherington et al. |
| 2006/0019360 A1 | 1/2006 | Verser et al. |
| 2006/0102520 A1 | 5/2006 | Lapinski et al. |
| 2006/0106246 A1 | 5/2006 | Warner et al. |
| 2006/0127999 A1 | 6/2006 | Verser et al. |
| 2007/0270511 A1 | 11/2007 | Melnichuk et al. |
| 2008/0207953 A1 | 8/2008 | Houssin et al. |
| 2009/0005588 A1 | 1/2009 | Hassan et al. |
| 2009/0023192 A1 | 1/2009 | Verser et al. |
| 2009/0081749 A1 | 3/2009 | Verser et al. |
| 2009/0166172 A1 | 7/2009 | Casey et al. |
| 2009/0221725 A1 | 9/2009 | Chornet et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029995 A1 | 2/2010 | Johnston et al. |
| 2010/0029996 A1 | 2/2010 | Danjo et al. |
| 2010/0113843 A1 | 5/2010 | Lee et al. |
| 2010/0121114 A1 | 5/2010 | Weiner et al. |
| 2010/0125148 A1 | 5/2010 | Johnston et al. |
| 2010/0168493 A1 | 7/2010 | Le Peltier et al. |
| 2010/0196789 A1 | 8/2010 | Fisher et al. |
| 2010/0249479 A1 | 9/2010 | Berg-Slot et al. |
| 2011/0004033 A1 | 1/2011 | Johnston et al. |
| 2011/0071312 A1 | 3/2011 | Johnston et al. |
| 2011/0282109 A1 | 11/2011 | Johnston et al. |
| 2012/0238785 A1 | 9/2012 | Zhou et al. |

FOREIGN PATENT DOCUMENTS

| | | | |
|---|---|---|---|
| CN | 102229520 | 11/2011 | |
| EP | 0104197 | 4/1984 | |
| EP | 0137749 A2 | 4/1984 | |
| EP | 0167300 A1 | 1/1986 | |
| EP | 0175558 | 3/1986 | |
| EP | 0192587 | 8/1986 | |
| EP | 0198682 B1 | 10/1986 | |
| EP | 0285786 B1 | 5/1988 | |
| EP | 0330853 | 9/1989 | |
| EP | 0400904 | 5/1990 | |
| EP | 0372847 A2 | 6/1990 | |
| EP | 0372847 A2 * | 6/1990 | ............. C07C 67/00 |
| EP | 0408528 | 7/1990 | |
| EP | 0407038 | 1/1991 | |
| EP | 0285420 B1 | 10/1991 | |
| EP | 0990638 | 4/2000 | |
| EP | 1262234 | 12/2002 | |
| EP | 1277826 | 1/2003 | |
| EP | 2060553 A1 | 5/2009 | |
| EP | 2060555 A1 | 5/2009 | |
| EP | 2186787 | 5/2010 | |
| GB | 1168785 | 10/1969 | |
| GB | 1559540 | 1/1980 | |
| GB | 2136704 | 9/1987 | |
| JP | 6-116182 | 4/1994 | |
| JP | 10-306047 A | 11/1998 | |
| JP | 11-147845 | 6/1999 | |
| JP | 2001-046874 A | 2/2001 | |
| JP | 2001-157841 A | 6/2001 | |
| WO | WO 83/03409 A1 | 10/1983 | |
| WO | WO 03/040037 A1 | 5/2003 | |
| WO | WO 2005/102513 | 11/2005 | |
| WO | WO 2009/009322 A1 | 1/2009 | |
| WO | WO 2009/009323 A1 | 1/2009 | |
| WO | WO 2009/063176 A1 | 5/2009 | |
| WO | WO 2009/086839 | 7/2009 | |
| WO | WO 2009/105860 A1 | 9/2009 | |
| WO | WO 2010/014145 A2 | 2/2010 | |
| WO | WO 2010/014151 | 2/2010 | |
| WO | WO 2010/014153 | 2/2010 | |
| WO | WO 2010/055285 | 5/2010 | |

(56) References Cited

FOREIGN PATENT DOCUMENTS

| WO | WO 2010/056299 | 5/2010 |
|---|---|---|
| WO | WO 2011/053365 | 5/2011 |
| WO | WO 2011/053367 | 5/2011 |

OTHER PUBLICATIONS

ZeaChem, Inc., Technology Overview, Lakewood, Colorado www.zeachem.com, 2008.
Brunauer Emmett and Teller, J. Am. Chem. Soc. 60, 309 (1938).
Proc. Roy Soc. A314, pp. 473-498 (1970).
International Search Report and Written Opinion for PCT/US2009/004197 mailed Mar. 24, 2010 (14 pages).
International Search Report and Written Opinion for PCT/US2009/004195 mailed Mar. 26, 2010 (12 pages).
Pestman et al., Reactions of Carboxylic Acids on Oxides, Journal of Catalysis 168:255-264 (1997).
Pestman et al., Identification of the Active Sites in the Selective Hydrogenation of Acetic Acid to Acetaldehyde on Iron Oxide Catalysts, Journal of Catalysis 174:142-152 (1998).
Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.
Santori et al. (2000). Hydrogenation of carbonylic compounds on Pt/SiO2 catalysts modified with SnBu4, Studies in Surface Science and Catalysis, 130, 2063-2068.
Acala, et al. (2005). Experimental and DFT studies of the conversion of ethanol and acetic acid on PtSn-based catalysts, Journal of Physical Chemistry, 109(6), 2074-2085.
International Search Report and Written Opinion for PCT/US2010/022949 mailed Jun. 7, 2010.
Subramani et al. "A Review of Recent Literature to Search for an Efficient Catalytic Process for the Conversion of Syngas to Ethanol," Energy & Fuels, 2008, vol. 22, pp. 814-839.
Nefedov and I V Mishin B K, "Synthesis of diethyl ether in presence of zeolite catalysts", Russian Chem. Bull., Springer Anew York LLC, v. 28, Jan. 1, 1979, pp. 183-186.
International Preliminary Report on Patentability mailed on May 18, 2012 in corresponding International Application No. PCT/US2010/054136.
International Search Report and Written Opinion mailed on May 22, 2012 in corresponding International Application No. PCT/US2012/031207.
Minglin Xiang et al., "XPS study of potassium-promoted molybdenum carbides for mixed alcohols synthesis via CO hydrogenation", Journal of Natural Gas Chemistry, vol. 19, 2010, pp. 151-155.
Jingfa D et al., "Acidic properties of ZSM-5 zeolite and conversion of ethanol to diethyl ether," Applied Catalyst, v. 41, Jan. 1, 1988, pp. 13-22.
International Search Report and Written Opinion mailed Feb. 28, 2011 in corresponding International Application No. PCT/US2010/054132.
International Written Opinion mailed on Nov. 29, 2011 in corresponding International Application No. PCT/US2010/054132.
International Preliminary Report on Patentability mailed Feb. 1, 2012 in corresponding International Application No. PCT/US2010/054132.
International Search Report and Written Opinion mailed Feb. 28, 2011 in corresponding International Application No. PCT/US2010/054134.
International Search Report and Written Opinion mailed Sep. 7, 2011 in corresponding International Application No. PCT/US2010/022950.
International Search Report and Written Opinion mailed Jun. 7, 2010 in corresponding International Application No. PCT/US2010/022947.
Invitation to Pay Fees and Partial International Search Report mailed Jun. 15, 2010 in corresponding International Application No. PCT/US2010/022950.
International Search Report and Written Opinion mailed Jun. 7, 2010 in corresponding International Application No. PCT/US2010/022953.
U.S. Office Action mailed Oct. 24, 2012 in co-pending U.S. Appl. No. 13/179,955.
U.S. Office Action mailed Oct. 15, 2012 in co-pending U.S. Appl. No. 12/850,414.
Djerboua, et al., "On the performance of a highly loadedCO/SiO2 catalyst in the gas phase hydrogenation of crotonaldehyde thermal treatments—catalyst structure-selectivity relationship," Applied Catalysis A: General (2005), 282, p. 123-133.
Liberkova, and Tourounde, "Performance of Pt/SnO2 catalyst in the gas phase hydrogenation of crotonaldehyde," J. Mol. Catal. A: Chemical (2002), 180, p. 221-230.
Rodrigues and Bueno, "Co/SiO2 catalysts for selective hydrogenation of crotonaldehyde: III. Promoting effect of zinc," Applied Catalysis A: General (2004), 257, p. 210-211.
Ammari, et al. "An emergent catalytic material: Pt/ZnO catalyst for selective hydrogenation of crotonaldehyde," J. Catal. (2004), 221, p. 32-42.
Ammari, et al. "Selective hydrogenation of crotonaldehyde on Pt/ZnCl2/SiO2 catalysts," J. Catal. (2005), 235, p. 1-9.
Consonni, et al. "High Performances of Pt/ZnO Catalysts in Selective Hydrogenation of Crotonaldehyde," J. Catal. (1999), 188, p. 165-175.
Nitta, et al. "Selective hydrogenation of $\alpha\beta$-unsaturated aldehydes on cobalt—silica catalysts obtained from cobalt chrysotile," Applied Catal. (1989), 56, p. 9-22.
International Search Report and Written Opinion for PCT/US2010/022949 mailed Jul. 6, 2010 (21 pages).
International Search Report and Written Opinion for PCT/US2010/054136 mailed May 25, 2011 (19 pages).
Spivey et al., "Heterogeneous catalytic synthesis of ethanol from biomass-derived syngas", Chemical Society Reviews, 2007, 36, pp. 1514-1528.
T. Yokoyama et al., "Fine chemicals through heterogeneous catalysis. Carboxylic acids and derivitatives." 2001, pp. 370-379.
English language abstract for CN 1230458 A, (Oct. 6, 1996).
English language abstract for JP 6116182 A. (Apr. 26, 1994).
English language abstract for JP 11-147845 A. (Jun. 2, 1996).

* cited by examiner

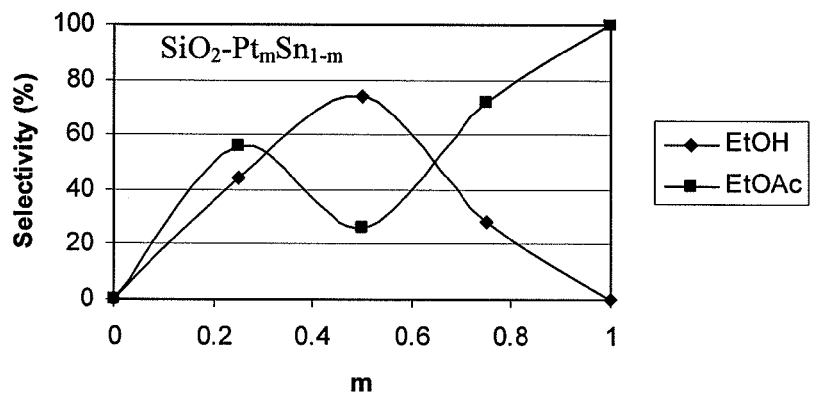
FIG. 1A - Selectivity Pt/Sn Catalyst
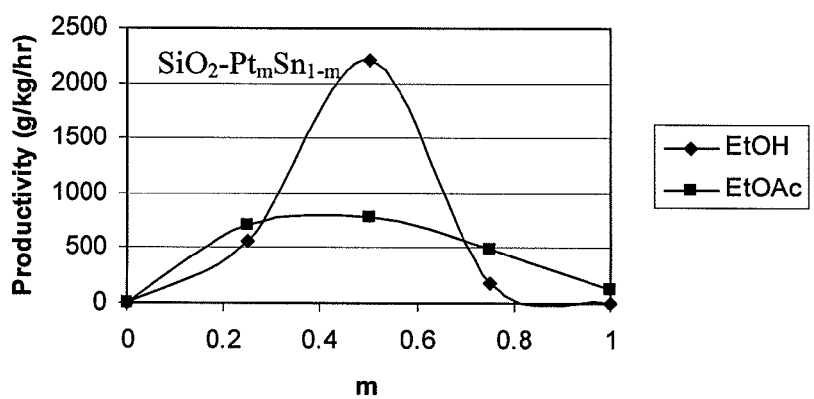
FIG. 1B - Productivity of Pt/Sn Catalyst
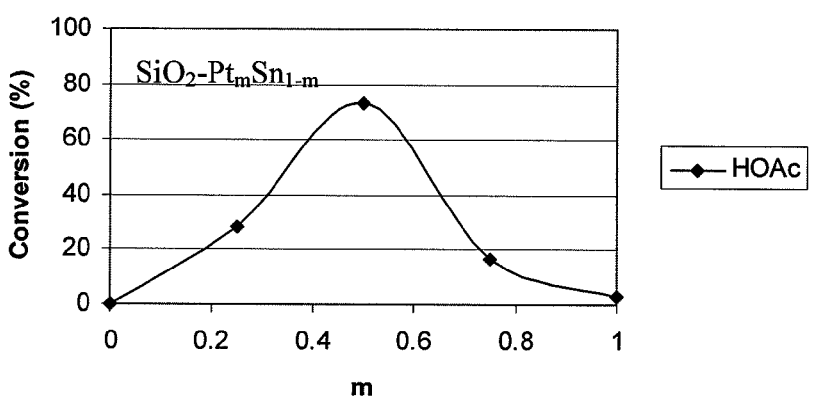
FIG. 1C - Conversion of HOAc

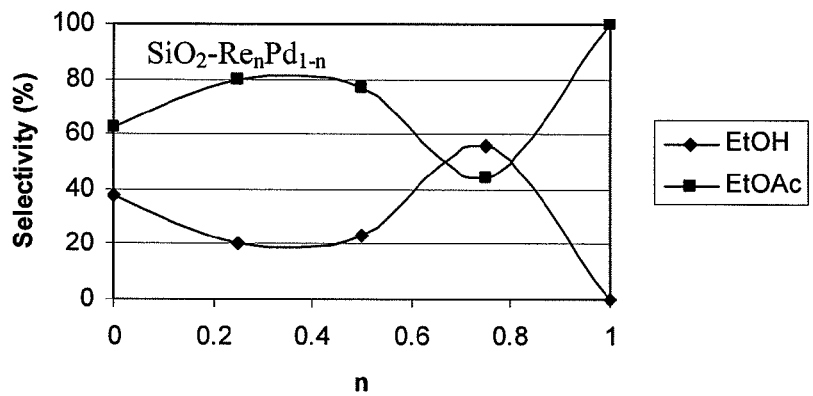
FIG. 2A - Selectivity of Re/Pd
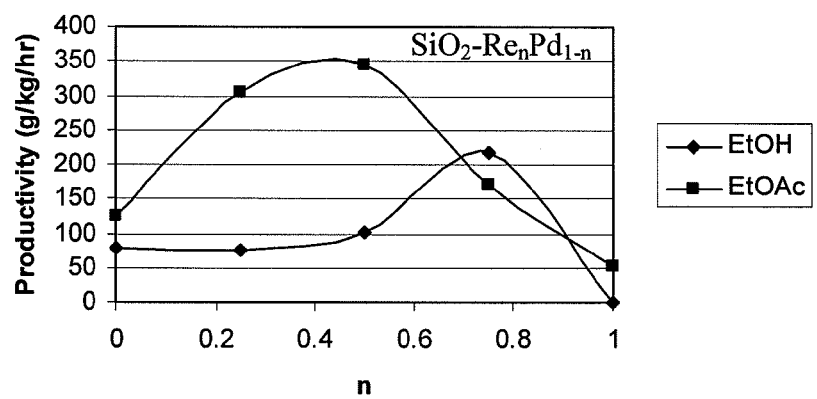
FIG. 2B - Productivity of Re/Pd
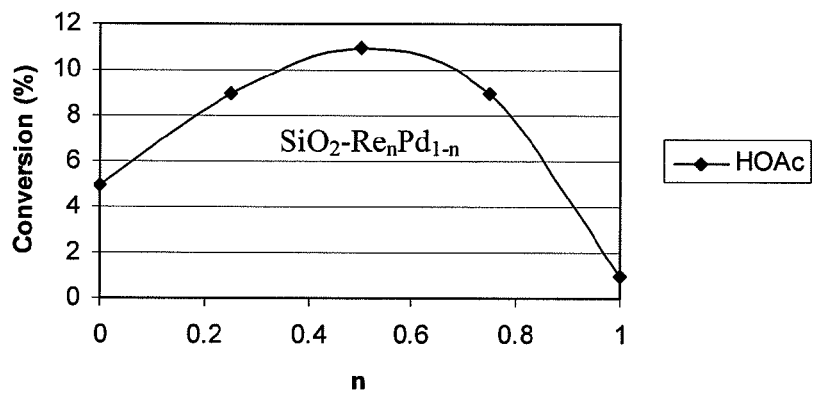
FIG. 2C - Conversion of HOAc

PROCESSES FOR MAKING ETHYL ACETATE FROM ACETIC ACID

CROSS REFERENCE TO RELATED APPLICATIONS

This is a continuation-in-part of U.S. application Ser. No. 12/588,727, filed Oct. 26, 2009, entitled "Tunable Catalyst Gas Phase Hydrogenation of Carboxylic Acids," of U.S. application Ser. No. 12/221,209, filed Jul. 31, 2008, entitled "Direct and Selective Production of Ethyl Acetate from Acetic Acid Utilizing a Bimetal Supported Catalyst," and of U.S. application Ser. No. 12/221,141, filed Jul. 31, 2008, entitled "Direct and Selective Production of Ethanol from Acetic Acid Utilizing a Platinum/Tin Catalyst," the entireties of which are incorporated herein by reference.

FIELD OF THE INVENTION

The present invention relates generally to processes for hydrogenating acetic acid to form ethyl acetate or a mixture of ethyl acetate and ethanol and to novel catalysts for use in such processes, the catalysts having high selectivities for ethyl acetate.

BACKGROUND OF THE INVENTION

There is a long felt need for an economically viable process to convert acetic acid to ethyl acetate. Ethyl acetate is an important commodity feedstock for a variety of industrial products and is also used as an industrial solvent in the manufacture of various chemicals. For instance, ethyl acetate can readily be converted to ethylene by subjecting it to a cracking process, which can then be converted to a variety of other products. Ethyl acetate is conventionally produced from feedstocks where price fluctuations are becoming more significant. That is, fluctuating natural gas and crude oil prices contribute to fluctuations in the cost of conventionally produced, petroleum or natural gas-sourced ethyl acetate, making the need for alternative sources of ethyl acetate all the greater when oil prices rise.

Ethanol is another important commodity chemical, which may be used in its own right, for example as a fuel, or as a feedstock for forming ethylene, vinyl acetate, ethyl acetate, or other chemical products. The hydrogenation of carboxylic acids over heterogeneous catalysts to produce alcohols is well reported. For instance, U.S. Pat. No. 2,607,807 discloses that ethanol can be formed from acetic acid over a ruthenium catalyst at extremely high pressures of 700-950 bar in order to achieve yields of around 88%, whereas low yields of only about 40% are obtained at pressures of about 200 bar. However such extreme reaction conditions are unacceptable and uneconomical for a commercial operation.

More recently, even though it may not still be commercially viable it has been reported that ethanol can be produced from hydrogenating acetic acid using a cobalt catalyst at superatmospheric pressures such as about 40 to 120 bar. See, for example, U.S. Pat. No. 4,517,391 to Shuster et al.

On the other hand, U.S. Pat. No. 5,149,680 to Kitson et al. describes a process for the catalytic hydrogenation of carboxylic acids and their anhydrides to alcohols and/or esters utilizing a platinum group metal alloy catalyst. The catalyst is comprised of an alloy of at least one noble metal of Group VIII of the Periodic Table and at least one metal capable of alloying with the Group VIII noble metal, admixed with a component comprising at least one of the metals rhenium, tungsten or molybdenum. Although it has been claimed therein that improved selectivity to a mixture of alcohol and its ester with the unreacted carboxylic acid is achieved over the prior art references it was still reported that 3 to 9 percent of alkanes, such as methane and ethane are formed as by-products during the hydrogenation of acetic acid to ethanol under their optimal catalyst conditions.

A slightly modified process for the preparation of ethyl acetate by hydrogenating acetic acid has been reported in EP 0 372 847. In this process, a carboxylic acid ester, such as for example, ethyl acetate is produced at a selectivity of greater than 50% while producing the corresponding alcohol at a selectivity less than 10% from a carboxylic acid or anhydride thereof by reacting the acid or anhydride with hydrogen at elevated temperature in the presence of a catalyst composition comprising as a first component at least one of Group VIII noble metal and a second component comprising at least one of molybdenum, tungsten and rhenium and a third component comprising an oxide of a Group IVB element. However, even the optimal conditions reported therein result in significant amounts of by-products including methane, ethane, acetaldehyde and acetone in addition to ethanol. In addition, the conversion of acetic acid is generally low and is in the range of about 5 to 40% except for a few cases in which the conversion reached as high as 80%.

From the foregoing it is apparent that existing processes do not have the requisite selectivity to ethyl acetate and/or ethanol, employ highly expensive catalysts or produce undesirable by-products such as methane and ethane. Thus, the need exists for forming ethyl acetate (and optionally ethanol) at high selectivity using a more economical catalyst, while minimizing the formation of undesirable byproducts.

SUMMARY OF THE INVENTION

The present invention relates to a process for producing ethyl acetate at high selectivities. In one embodiment, the process comprises hydrogenating acetic acid in the presence of a catalyst under conditions effective to form ethyl acetate, wherein the catalyst comprises a first metal, a second metal and a support, wherein the first metal is selected from the group consisting of nickel, palladium and platinum, and is present in an amount greater than 1 wt %, based on the total weight of the catalyst. The second metal may be selected from the group consisting of molybdenum, rhenium, zirconium, copper, cobalt, tin, and zinc. The first metal may be present, for example, in an amount of from 0.1 to 10 wt. % and the second metal may be present in an amount of from 0.1 to 10 wt. %, based on the total weight of the catalyst.

In another embodiment, the present invention relates to a process for producing ethyl acetate, comprising hydrogenating acetic acid in the presence of a catalyst under conditions effective to form ethyl acetate, wherein the catalyst comprises a first metal, a second metal and a support, wherein the first metal is selected from group consisting of nickel and palladium, and wherein the second metal is selected from the group consisting of tin and zinc. In one embodiment, the first metal is present in an amount from 0.1 to 25 wt. %, based on the total weight of the catalyst.

In another embodiment, the present invention relates to a process for producing ethyl acetate comprising hydrogenating acetic acid in the presence of a catalyst under conditions effective to form ethyl acetate, wherein the catalyst comprises a first metal, a support, and at least one support modifier selected from the group of oxides of Group IVB metals, oxides of Group VB metals, oxides of Group VIB metals, iron oxides, aluminum oxides and mixtures thereof. As an example, the first metal may be present in an amount from 0.1 to 25 wt %, based on the total weight of the catalyst. In one aspect, the first metal is selected from the group consisting of Group IB, IIB, IIIB, IVB, VB, VIIB, VIIB, or VIII transitional metal, a lanthanide metal, an actinide metal or a metal from any of Groups IIIA, IVA, VA, or VIA. As another option, the first metal may be selected from the group consisting of copper, iron, cobalt, nickel, ruthenium, rhodium, palladium, osmium, iridium, platinum, titanium, zinc, chromium, rhenium, molybdenum, and tungsten. In another embodiment, the catalyst further comprises a second metal (optionally different from the first metal). In embodiments where a second metal is present, the second metal may be different from the first metal and may be selected from the group consisting of copper, molybdenum, tin, chromium, iron, cobalt, vanadium, tungsten, palladium, platinum, lanthanum, cerium, manganese, ruthenium, rhenium, gold, and nickel. Preferably, the first metal is platinum and/or the second metal is tin. In another preferred combination, the first metal is palladium and the second metal is rhenium. Optionally, the catalyst further comprises a third metal different from the first and second metals. The third metal may be selected from the group consisting of cobalt, palladium, ruthenium, copper, zinc, platinum, tin, and rhenium and/or may be present in an amount of 0.05 and 4 wt. %, based on the total weight of the catalyst.

As noted above, the catalysts may, generally, be suitable for use as a hydrogenation catalyst in converting acetic acid to ethyl acetate and at least 10% of the acetic acid may be converted during hydrogenation. Also, the hydrogenation may be performed in a vapor phase at a temperature of from 125° C. to 350° C., a pressure of 10 KPa to 3000 KPa, and a hydrogen to acetic acid mole ratio of greater than 4:1. In addition, the catalysts may have a selectivity to ethyl acetate of at least 40% and/or a selectivity to methane, ethane, and carbon dioxide of less than 4%. In one embodiment, the catalyst has a productivity that decreases less than 6% per 100 hours of catalyst usage.

In one embodiment, the support is present in an amount of 25 wt. % to 99 wt. %, based on the total weight of the catalyst and is selected from the group consisting of iron oxide, silica, alumina, silica/aluminas, titania, zirconia, magnesium oxide, calcium silicate, carbon, graphite, high surface area graphitized carbon, activated carbons, and mixtures thereof. As one option, the catalyst may comprise at least one support modifier selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof preferably being $CaSiO_3$. In another option the support modifier is selected from the group consisting of oxides of Group IVB metals, oxides of Group VB metals, oxides of Group VIB metals, iron oxides, aluminum oxides and mixtures thereof. The support modifier may be present in an amount of 0.1 wt. % to 50 wt. %, based on the total weight of the catalyst.

In another embodiment, the invention relates to a crude product (optionally obtained from the hydrogenation of acetic acid, as discussed herein), which comprises (a) ethyl acetate in an amount from 5 to 70 wt. %; (b) ethanol in an amount from 5 to 70 wt. %; (c) acetic acid in an amount from 5 to 75 wt. %; (d) water in an amount of from 5 to 50 wt %; and (e) any other compounds in an amount less than 10 wt %, wherein all weight percents are based on the total weight of the crude product. A preferred crude ethanol product comprises (a) ethyl acetate in an amount from 15 to 50 wt. %; (b) ethanol in an amount from 5 to 70 wt. %; (c) acetic acid in an amount from 10 to 60 wt. %; (d) water in an amount of from 10 to 45 wt %; and (e) any other compounds in an amount less than 6 wt %, wherein all weight percents are based on the total weight of the crude product.

BRIEF DESCRIPTION OF DRAWINGS

The invention is described in detail below with reference to the appended drawings, wherein like numerals designate similar parts.

FIG. 1A is a graph of the selectivity to ethanol and ethyl acetate using a $SiO_2$—$Pt_mSn_{1-m}$ catalyst;

FIG. 1B is a graph of the productivity to ethanol and ethyl acetate of the catalyst of FIG. 1A;

FIG. 1C is a graph of the conversion of the acetic acid of the catalyst of FIG. 1A;

FIG. 2A is a graph of the selectivity to ethanol and ethyl acetate using a $SiO_2$—$Re_nPd_{1-n}$ catalyst;

FIG. 2B is a graph of the productivity to ethanol and ethyl acetate of the catalyst of FIG. 2A;

FIG. 2C is a graph of the conversion of the acetic acid of the catalyst of FIG. 2A;

DETAILED DESCRIPTION OF THE INVENTION

Introduction

Figure 3:
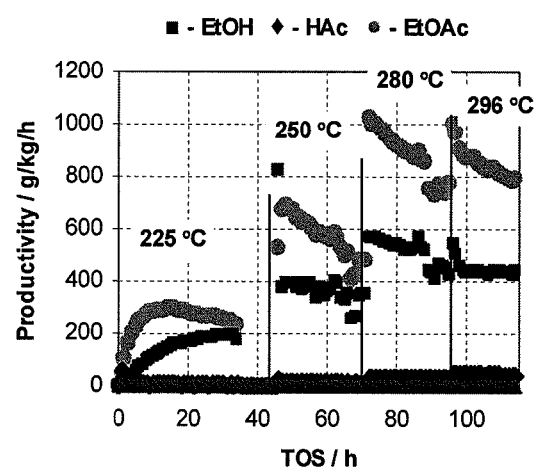
FIG. 3 is a graph of the activity of a catalyst compared to the productivity of the catalyst to a mixture of ethyl acetate and ethanol at various temperatures according to one embodiment of the invention.

The present invention relates to processes for producing ethyl acetate by hydrogenating acetic acid in the presence of a catalyst. The hydrogenation reaction may be represented as follows:

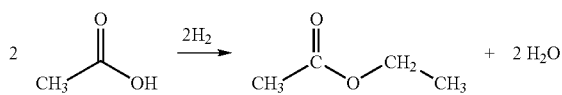

Depending on the catalyst and process conditions employed, the hydrogenation reaction may produce ethanol in addition to ethyl acetate. Embodiments of the present invention beneficially may be used in industrial applications to produce ethyl acetate and/or ethanol on an economically feasible scale.

The processes of the invention employ various catalysts that may be used to form ethyl acetate and optionally ethanol. Typically, the catalyst will comprises a first metal and optionally one or more of a second metal, a third metal, and optionally additional metals. The one or more metals preferably are disposed on a support, such as silica or titania. In a first embodiment, the process employs a catalyst that includes a high loading of nickel, palladium or platinum. In a second embodiment, the process employs a catalyst that comprises a first metal selected from nickel and palladium and a second metal selected from tin and zinc. In a third embodiment, the process employs a catalyst that comprises one or more metals on a support that has been modified with an acidic support modifier or a redox support modifier. It has now been discovered that these catalyst compositions surprisingly and unexpectedly can be formulated to be selective for the formation of ethyl acetate, optionally in combination with ethanol.

High Loading Nickel, Palladium and Platinum Catalysts

In a first embodiment, the invention is to hydrogenation processes using catalysts that comprise one or more of nickel, palladium or platinum at high metal loadings. For example, the catalyst may comprise a first metal selected from the group consisting of nickel, palladium, and platinum on a support in an amount greater than 1 wt. %, e.g., greater than 1.1 wt. %, or greater than 1.2 wt. %, based on the total weight of the catalyst. In terms of ranges, the amount of the first metal on the support preferably is from 1 to 25 wt. %, e.g., from 1.2 to 15 wt. %, or from 1.5 wt. % to 10 wt. %. For purposes of the present specification, unless otherwise indicated, weight percent is based on the total weight the catalyst including metal and support.

The metal(s) in the catalyst may be present in the form of one or more elemental metals and/or one or more metal oxides. For purposes of determining the weight percent of the metal(s) in the catalyst, the weight of any oxygen that is bound to the metal is ignored. In a more preferred aspect, the first metal is selected from platinum and palladium. When the first metal comprises platinum, it is preferred that the catalyst comprises the platinum in an amount greater than 1 wt. %, but less than 10 wt. %, e.g., less than 5 wt. % or less than 3 wt. %, due to the availability of platinum.

In addition to the first metal, the catalyst optionally further comprises one or more of a second metal, a third metal or additional metals. In this context, the numerical terms "first," "second," "third," etc., when used to modify the word "metal," are meant to indicate that the respective metals are different from one another. If present, the second metal preferably is selected from the group consisting of molybdenum, rhenium, zirconium, copper, cobalt, tin, and zinc. More preferably, the second metal is selected from the group consisting of molybdenum, rhenium, tin and cobalt. Even more preferably, the second metal is selected from tin and rhenium.

Where the catalyst includes two or more metals, one metal may act as a promoter metal and the other metal is the main metal. For instance, with a platinum/tin catalyst, platinum may be considered to be the main metal and tin may be considered the promoter metal. For convenience, the present specification refers to the first metal as the primary catalyst and the second metal (and optional metals) as the promoter(s). This should not be taken as an indication of the underlying mechanism of the catalytic activity.

In the first embodiment, when the catalyst includes two or more metals, e.g., a first metal and a second metal, the first metal optionally is present in the catalyst in an amount from 1 to 10 wt. %, e.g., from 1.2 to 5 wt. %, or from 1.5 to 3 wt. %. The second metal optionally is present in an amount from 0.1 and 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary somewhat depending on the metals used in the catalyst. In some embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

Molar ratios other than 1:1 may be preferred depending on the composition of the catalyst employed. It has now surprisingly and unexpectedly been discovered, for example, that for platinum/tin catalysts, platinum to tin molar ratios less than 0.4:0.6, or greater than 0.6:0.4 are particularly preferred in order to form ethyl acetate from acetic acid at high selectivity, conversion and productivity, as shown in FIGS. 1A, 1B and 1C. More preferably, the Pt/Sn ratio is greater than 0.65:0.35 or greater than 0.7:0.3, e.g., from 0.65:0.35 to 1:0 or from 0.7:0.3 to 1:0. Selectivity to ethyl acetate may be further improved by incorporating modified supports as described herein.

With rhenium/palladium catalysts, as shown in FIGS. 2A, 2B and 2C, preferred rhenium to palladium molar ratios for forming ethyl acetate in terms of selectivity, conversion and production are less than 0.7:0.3 or greater than 0.85:0.15. A preferred Re/Pd ratio for producing ethyl acetate in the presence of a Re/Pd catalyst is from 0.2:0.8 to 0.4:0.6. Again, selectivity to ethyl acetate may be further improved by incorporating modified supports as described herein.

In embodiments when the catalyst comprises a third metal, the third metal may be selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When the third metal is present, the catalyst composition preferably comprises the third metal in an amount from 0.05 and 4 wt. %, e.g., from 0.1 to 3 wt. %, or from 0.1 to 2 wt. %.

In addition to the metal, the catalysts of the first embodiment further comprise a support, optionally a modified support. As will be appreciated by those of ordinary skill in the art, support materials are selected such that the catalyst system is suitably active, selective and robust under the process conditions employed for the formation of ethyl acetate or a mixture of ethyl acetate and ethanol. Suitable support materials may include, for example, stable metal oxide-based supports or ceramic-based supports as well as molecular sieves, such as zeolites. Examples of suitable support materials include without limitation, iron oxide, silica, alumina, silica/aluminas, titania, zirconia, magnesium oxide, calcium silicate, carbon, graphite, high surface area graphitized carbon, activated carbons, and mixtures thereof. Exemplary preferred supports are selected from the group consisting of silica/aluminas, titania, and zirconia. The total weight of the support in the catalyst, based on the total weight of the catalyst, preferably is from 25 wt % to 99 wt %, e.g., from 30 wt % to 98.5 wt %, or from 35 wt % to 98 wt %.

A preferred silica/alumina support material is KA-160 (Sud Chemie) silica spheres having a nominal diameter of about 5 mm, a density of about 0.562 g/ml, in absorptivity of about 0.583 g $H_2O$/g support, a surface area of about 160 to 175 $m^2$/g, and a pore volume of about 0.68 ml/g.

In one embodiment, the support material comprises a siliceous support material selected from the group consisting of silica, silica/alumina, a Group IIA silicate such as calcium metasilicate, pyrogenic silica, high purity silica and mixtures thereof. In one embodiment silica may be used as the siliceous support, and the amount of aluminum, which is a common contaminant for silica, may be low, preferably under 1 wt. %, e.g., under 0.5 wt. % or under 0.3 wt. %, based on the total weight of the support. In this regard, pyrogenic silica is preferred as it commonly is available in purities exceeding 99.7 wt. %. High purity silica, as used throughout the application, refers to silica in which acidic contaminants such as aluminum are present, if at all, at levels of less than 0.3 wt. %, e.g., less than 0.2 wt. % or less than 0.1 wt. %.

The surface area of the support may vary widely depending on the type of support. In some aspects, the surface area of the support material, e.g., siliceous material, may be at least about 50 $m^2$/g, e.g., at least about 100 $m^2$/g, at least about 150 $m^2$/g, at least about 200 $m^2$/g or most preferably at least about 250 m²/g. In terms of ranges, the support material preferably has a surface area of from 50 to 600 m²/g, e.g., from 100 to 500 m²/g or from 100 to 300 m²/g. High surface area silica, as used throughout the application, refers to silica having a surface area of at least about 250 m²/g. High surface area silica/alumina, as used throughout the application, refers to silica/alumina having a surface area of at least about 150 m²/g. For purposes of the present specification, surface area refers to BET nitrogen surface area, meaning the surface area as determined by ASTM D6556-04, the entirety of which is incorporated herein by reference.

The support material, e.g. silicaceous material, also preferably has an average pore diameter of from 5 to 100 nm, e.g., from 5 to 30 nm, from 5 to 25 nm or from about 5 to 10 nm, as determined by mercury intrusion porosimetry, and an average pore volume of from 0.5 to 2.0 cm³/g, e.g., from 0.7 to 1.5 cm³/g or from about 0.8 to 1.3 cm³/g, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the support material, e.g., silicaceous material, has a morphology that allows for a packing density of from 0.1 to 1.0 g/cm³, e.g., from 0.2 to 0.9 g/cm³ or from 0.5 to 0.8 g/cm³. In terms of size, the support material, e.g. silicaceous material, preferably has an average particle size, meaning the diameter for spherical particles or equivalent spherical diameter for non-spherical particles, of from 0.01 to 1.0 cm, e.g., from 0.1 to 0.5 cm or from 0.2 to 0.4 cm. Since the one or more metal(s) that are disposed on or within the modified support are generally very small in size, they should not substantially impact the size of the overall catalyst particles. Thus, the above particle sizes generally apply to both the size of the modified supports as well as to the final catalyst particles.

A preferred silica support material is SS61138 High Surface Area (HSA) Silica Catalyst Carrier from Saint Gobain N or Pro. The Saint-Gobain N or Pro SS61138 silica contains approximately 95 wt % high surface area silica; a surface area of about 250 m²/g; a median pore diameter of about 12 nm; a total pore volume of about 1.0 cm³/g as measured by mercury intrusion porosimetry and a packing density of about 0.352 g/cm³ (22 lb/ft³).

The supports for the first embodiment may further comprise a support modifier. A support modifier is added to the support and is not naturally present in the support. A support modifier adjusts effects of the acidity of the support material. The acid sites, e.g. Brønsted acid sites, on the support material may be adjusted by the support modifier, for example, to favor selectivity to ethyl acetate and mixtures of ethyl acetate during the hydrogenation of acetic acid. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference.

In some aspects, the support material may be undesirably too acidic for formation of ethyl acetate at high selectivity. In this case, the support material may be modified with a basic support modifier. Suitable basic support modifiers may be selected, for example, from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used in embodiments of the present invention. Preferably, the basic modifiers have a low volatility or are non-volatile. Low volatility modifiers have a rate of loss that is low enough such that the acidity of the support modifier is not reversed during the life of the catalyst. For example, the support modifier may be selected from the group consisting of oxides and metasilicates of any of sodium, potassium, magnesium, calcium, scandium, yttrium, and zinc, and mixtures of any of the foregoing. A particularly preferred basic support modifier is calcium metasilicate (CaSiO₃).

In some aspects, the support material is too basic or is not acidic enough for formation of ethyl acetate at high selectivity. In this case, the support may be modified with a support modifier that adjusts the support material by increasing the number or availability of acid sites by using a redox support modifier or an acidic support modifier. Suitable redox and acidic support modifiers may be selected from the group consisting of: oxides of Group IVB metals, oxides of Group VB metals, oxides of Group VIB metals, iron oxides, aluminum oxides, and mixtures thereof. These support modifiers are redox or acid non-volatile support modifiers. Preferred redox support modifiers include those selected from the group consisting of $WO_3$, $MoO_3$, $Fe_2O_3$, and $Cr_2O_3$. Preferred acidic support modifiers include those selected from the group consisting of $TiO_2$, $ZrO_2$, $Nb_2O_5$, $Ta_2O_5$, and $Al_2O_3$. Without being bound by theory, it is believed that an increase in acidity of the support may favor ethyl acetate formation. However, increasing acidity of the support may also form ethers and basic modifiers may be added to counteract the acidity of the support.

Catalysts Comprising Nickel or Palladium and Tin or Zinc

In a second embodiment of the present invention, the invention is to a hydrogenation process that employs a catalyst for making ethyl acetate or optionally a mixture of ethyl acetate and ethanol, in which the catalyst comprises a first metal selected from the group consisting of nickel and palladium, a second metal selected from the group consisting of tin and zinc, and a support, optionally a modified support. In contrast to the above-described first embodiment, in the second embodiment, lower loadings of the first metal may be employed. For example, the catalyst may comprise the first metal in an amount from 0.1 to 10 wt. %, e.g., from 0.1 to 5 wt. %, or from 0.1 to 3 wt. %. The second metal preferably is present in an amount from 0.1 and 20 wt. %, e.g., from 0.1 to 10 wt. %, or from 0.1 to 5 wt. %. The mole ratio of the first metal to the second metal preferably is from 10:1 to 1:10, e.g., from 4:1 to 1:4, from 2:1 to 1:2, from 1.5:1 to 1:1.5 or from 1.1:1 to 1:1.1. Optionally, the catalyst of the second embodiment may further comprise a third metal as described above in connection with the first embodiment.

In the second embodiment, the catalyst includes a support, optionally a modified support, as discussed above in connection with the first embodiment. The total weight of the support, based on the total weight of the catalyst, for the second embodiment preferably is from 25 wt. % to 99.9 wt. %, e.g., from 30 wt. % to 97 wt. %, or from 35 wt. % to 95 wt. %.

Catalyst on Acidic or Redox Modified Support

In a third embodiment of the invention, the hydrogenation process uses a catalyst that comprises a first metal and optionally one or more of a second metal, a third metal or additional metals, on a support that has been modified with a redox support modifier or an acidic support modifier. The total weight of all metals present in the catalyst preferably is from 0.1 to 25 wt. %, e.g., from 0.1 to 15 wt. %, or from 0.1 1 to 10 wt. %.

The first metal may be a Group IB, IIB, IIIB, IVB, VB, VIIB, VIIB, or VIII transitional metal, a lanthanide metal, an actinide metal or a metal from any of Groups IIIA, IVA, VA, or VIA. In a preferred embodiment, the first metal is selected the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. When the first metal comprises platinum, it is preferred that the catalyst comprises the platinum in an amount less than 5 wt %, e.g. less than 3 wt % or less than 1 wt %, due to the limited availability of platinum.

The catalyst optionally further comprises a second metal selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

If the catalyst includes two or more metals, e.g., a first metal and a second metal, the first metal optionally is present in the catalyst in an amount from 0.1 to 10 wt. %, e.g. from 0.1 to 5 wt. %, or from 0.1 to 3 wt. %. The second metal preferably is present in an amount from 0.1 and 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

As stated above in the first embodiment, in the third embodiment the preferred metal ratios may vary somewhat depending on the metals used in the catalyst. In some embodiments, the mole ratio of the first metal to the second metal preferably is from 10:1 to 1:10, e.g., from 4:1 to 1:4, from 2:1 to 1:2, from 1.5:1 to 1:1.5 or from 1.1:1 to 1:1.1.

Molar ratios other than 1:1 may be preferred for other catalysts. It has now surprisingly and unexpectedly been discovered, for example, that for platinum/tin catalysts, platinum to tin molar ratios less than 0.4:0.6, or greater than 0.6:0.4 are particularly preferred in order to form ethyl acetate from acetic acid at high selectivity, conversion and productivity, as shown in FIGS. 1A, 1B and 1C. A preferred Pt/Sn molar ratio for producing ethyl acetate in the presence of a Pt/Sn catalyst is from 0.65:0.35 to 0.95:0.05, e.g., from 0.7:0.3 to 0.95:0.05. Selectivity to ethyl acetate may be further improved by incorporating modified supports as described throughout the present specification.

With rhenium/palladium catalysts, as shown in FIGS. 2A, 2B and 2C, preferred rhenium to palladium molar ratios for forming ethyl acetate in terms of selectivity, conversion and production are less than 0.7:0.3 or greater than 0.85:0.15. A preferred Re/Pd molar ratio for producing ethyl acetate in the presence of a Re/Pd catalyst is from 0.2:0.8 to 0.4:0.6. Again, selectivity to ethyl acetate may be further improved by incorporating modified supports as described throughout the present specification.

In embodiments when the catalyst comprises a third metal, the third metal may be selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 and 4 wt. %, e.g., from 0.1 to 3 wt. %, or from 0.1 to 2 wt. %.

In one embodiment, the catalyst comprises a first metal and no additional metals (no second metal, etc.). In this embodiment, the first metal preferably is present in an amount from 0.1 to 10 wt. %. In another embodiment, the catalyst comprises a combination of two or more metals on a support. Specific preferred metal compositions for various catalysts of this embodiment of the invention are provided below in Table 1. Where the catalyst comprises a first metal and a second metal, the first metal preferably is present in an amount from 0.1 to 5 wt. % and the second metal preferably is present in an amount from 0.1 to 5 wt. %. Where the catalyst comprises a first metal, a second metal and a third metal, the first metal preferably is present in an amount from 0.1 to 5 wt. %, the second metal preferably is present in an amount from 0.1 to 5 wt. %, and the third metal preferably is present in an amount from 0.1 to 2 wt. %. Where the first metal is platinum, the first metal preferably is present in an amount from 0.1 to 3 wt. %, the second metal is present in an amount from 0.1 to 5 wt. %, and the third metal, if present, preferably is present in an amount from 0.1 to 2 wt. %.

TABLE 1

EXEMPLARY METAL COMBINATIONS FOR CATALYSTS

| First Metal | Second Metal | Third Metal |
|---|---|---|
| Cu | Ag | |
| Cu | Cr | |
| Cu | V | |
| Cu | W | |
| Cu | Zn | |
| Ni | Au | |
| Ni | Re | |
| Ni | V | |
| Ni | W | |
| Ni | Zn | |
| Ni | Sn | |
| Pd | Zn | |
| Pd | Co | |
| Pd | Cr | |
| Pd | Cu | |
| Pd | Fe | |
| Pd | La | |
| Pd | Mo | |
| Pd | Ni | |
| Pd | Re | |
| Pd | Sn | |
| Pd | V | |
| Pd | W | |
| Pt | Co | |
| Pt | Cr | |
| Pt | Cu | |
| Pt | Fe | |
| Pt | Mo | |
| Pt | Sn | |
| Pt | Sn | Co |
| Pt | Sn | Re |
| Pt | Sn | Ru |
| Pt | Sn | Pd |
| Rh | Cu | |
| Rh | Ni | |
| Ru | Co | |
| Ru | Cr | |
| Ru | Cu | |
| Ru | Fe | |
| Ru | La | |
| Ru | Mo | |
| Ru | Ni | |
| Ru | Sn | |

Depending primarily on how the catalyst is manufactured, the metals of the catalysts of the present invention may be dispersed throughout the support, coated on the outer surface of the support (egg shell) or decorated on the surface of the support.

In addition to one or more metals, the catalysts of the third embodiment of the present invention further comprise a modified support, meaning a support that includes a support material and a support modifier. In particular, the use of acidic or redox modified supports surprisingly and unexpectedly has now been demonstrated to favor formation of ethyl acetate over other hydrogenation products.

Examples of suitable support materials include those stated above in connection with the first embodiment and without limitation include iron oxide, silica, alumina, silica/aluminas, titania, zirconia, magnesium oxide, calcium silicate, carbon, graphite, high surface area graphitized carbon, activated carbons, and mixtures thereof. The support further comprises a support modifier that, for example, may be selected from the group consisting of: oxides of Group IVB metals, oxides of Group VB metals, oxides of Group VIB metals, iron oxides, aluminum oxides, and mixtures thereof. These support modifiers are redox or acidic support modifiers. Preferred redox support modifiers include those selected from the group consisting of $WO_3$, $MoO_3$, $Fe_2O_3$, and $Cr_2O_3$. Preferred acidic support modifiers include those selected from the group consisting of $TiO_2$, $ZrO_2$, $Nb_2O_5$, $Ta_2O_5$, and $Al_2O_3$. Preferably, the support comprises a support modifier that is an acidic or redox modifier having a low volatility or is non-volatile. Low volatility modifiers have a rate of loss that is low enough such that the acidity of the support modifier is not reversed during the life of the catalyst. As indicated above, the support modifier is added to the support and is not naturally present in the support.

The total weight of the modified support, including the support material and the support modifier, based on the total weight of the catalyst, preferably is from 25 wt. % to 99.9 wt. %, e.g., from 30 wt. % to 97 wt. %, or from 35 wt % to 95 wt. %. The support modifier preferably is provided in an amount sufficient to increase the number of active Brønsted acid sites or availability of those acid sites. In preferred embodiments, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst. In preferred embodiments, the support material is present in an amount from 25 wt. % to 99 wt. %, e.g., from 30 wt. % to 97 wt. % or from 35 wt. % to 95 wt. %.

If desired, the acidic or redox support modifiers described herein in connection with the third embodiment of the invention may also be used to modify the supports of the above-described first embodiment or the second embodiment.

Catalysts of the present invention are particulate catalysts in the sense that, rather than being impregnated in a wash coat onto a monolithic carrier similar to automotive catalysts and diesel soot trap devices, the catalysts of the invention preferably are formed into particles, sometimes also referred to as beads or pellets, having any of a variety of shapes and the catalytic metals are provided to the reaction zone by placing a large number of these shaped catalysts in the reactor. Commonly encountered shapes include extrudates of arbitrary cross-section taking the form of a generalized cylinder in the sense that the generators defining the surface of the extrudate are parallel lines. As indicated above, any convenient particle shape including pellets, extrudates, spheres, spray dried microspheres, rings, pentarings, trilobes, quadrilobes and multi-lobal shapes may be used, although cylindrical pellets are preferred. Typically, the shapes are chosen empirically based upon perceived ability to contact the vapor phase with the catalytic agents effectively.

One advantage of catalysts of the present invention, in all of the above embodiments, is the stability or activity of the catalyst for producing ethyl acetate and mixtures of ethyl acetate and ethanol. Accordingly, it can be appreciated that the catalysts of the present invention are fully capable of being used in commercial scale industrial applications for the hydrogenation of acetic acid, particularly in the production of ethyl acetate. In particular, it is possible to achieve such a degree of stability such that catalyst activity will have rate of productivity decline that is less than 6% per 100 hours of catalyst usage, e.g., less than 3% per 100 hours or less than 1.5% per 100 hours. Preferably, the rate of productivity decline is determined once the catalyst has achieved steady-state conditions.

Processes for Making the Catalysts

The catalyst compositions of the first, second and third embodiments of the present invention preferably are formed through metal impregnation of the support and/or modified supports, although other processes such as chemical vapor deposition may also be employed. Before the metals are impregnated, it typically is desired to form the modified support, if necessary, through a step of impregnating the support material with the support modifier. In one aspect, the support modifier, e.g., $WO_3$ or $TiO_2$, or a precursor to the support modifier is added to the support material in an aqueous suspension. For example, an aqueous suspension of the support modifier may be formed by adding the solid support modifier to deionized water, followed by the addition of colloidal support material thereto. The resulting mixture may be stirred and added to additional support material using, for example, incipient wetness techniques in which the support modifier is added to a support material having the same pore volume as the volume of the support modifier solution. Capillary action then draws the support modifier into the pores in the support material. The modified support can then be formed by drying and calcining to drive off water and any volatile components within the support modifier solution and depositing the support modifier on the support material. Drying may occur, for example, at a temperature of from 50° C. to 300° C., e.g., from 100° C. to 200° C. or about 120° C., optionally for a period of from 1 to 24 hours, e.g., from 3 to 15 hours or from 6 to 12 hours. Once formed, the modified supports may be shaped into particles having the desired size distribution, e.g., to form particles having an average particle size in the range of from 0.2 to 0.4 cm. The supports may be extruded, pelletized, tabletized, pressed, crushed or sieved to the desired size distribution. Any of the known methods to shape the support materials into desired size distribution can be employed. Calcining of the shaped modified support may occur, for example, at a temperature of from 250° C. to 800° C., e.g., from 300 to 700° C. or about 500° C., optionally for a period of from 1 to 12 hours, e.g., from 2 to 10 hours, from 4 to 8 hours or about 6 hours.

In a preferred method of preparing the catalyst, the metals are impregnated onto the support or modified support. A precursor of the first metal (first metal precursor) preferably is used in the metal impregnation step, such as a water soluble compound or water dispersible compound/complex that includes the first metal of interest. Depending on the metal precursor employed, the use of a solvent, such as water, glacial acetic acid or an organic solvent, may be preferred. The second metal also preferably is impregnated into the support or modified support from a second metal precursor. If desired, a third metal or third metal precursor may also be impregnated into the support or modified support.

Impregnation occurs by adding, optionally drop wise, either or both the first metal precursor and/or the second metal precursor and/or additional metal precursors, preferably in suspension or solution, to the dry support or modified support. The resulting mixture may then be heated, e.g., optionally under vacuum, in order to remove the solvent. Additional drying and calcining may then be performed, optionally with ramped heating to form the final catalyst composition. Upon heating and/or the application of vacuum, the metal(s) of the metal precursor(s) preferably decompose into their elemental (or oxide) form. In some cases, the completion of removal of the liquid carrier, e.g., water, may not take place until the catalyst is placed into use and calcined, e.g., subjected to the high temperatures encountered during operation. During the calcination step, or at least during the initial phase of use of the catalyst, such compounds are converted into a catalytically active form of the metal or a catalytically active oxide thereof.

Impregnation of the first and second metals (and optional additional metals) into the support or modified support may occur simultaneously (co-impregnation) or sequentially. In simultaneous impregnation, the first and second metal precursors (and optionally additional metal precursors) are mixed together and added to the support or modified support together, followed by drying and calcination to form the final catalyst composition. With simultaneous impregnation, it may be desired to employ a dispersion agent, surfactant, or solubilizing agent, e.g., ammonium oxalate, to facilitate the dispersing or solubilizing of the first and second metal precursors in the event the either or both precursors are incompatible with the desired solvent, e.g., water.

In sequential impregnation, the first metal precursor is first added to the support or modified support followed by drying and calcining, and the resulting material is then impregnated with the second metal precursor followed by an additional drying and calcining step to form the final catalyst composition. Additional metal precursors (e.g., a third metal precursor) may be added either with the first and/or second metal precursor or a separate third impregnation step, followed by drying and calcination. Of course, combinations of sequential and simultaneous impregnation may be employed if desired.

Suitable metal precursors include, for example, metal halides, amine solubilized metal hydroxides, metal nitrates or metal oxalates of the desired metal(s). For example, suitable compounds for platinum precursors and palladium precursors include chloroplatinic acid, ammonium chloroplatinate, amine solubilized platinum hydroxide, platinum nitrate, platinum tetra ammonium nitrate, platinum chloride, platinum oxalate, palladium nitrate, palladium tetra ammonium nitrate, palladium chloride, palladium oxalate, sodium palladium chloride, and sodium platinum chloride. Generally, both from the point of view of economics and environmental aspects, aqueous solutions of soluble compounds of platinum are preferred. In one embodiment, the first metal precursor is not a metal halide and is substantially free of metal halides.

In one aspect, the "promoter" metal or metal precursor is first added to the modified support, followed by the "main" or "primary" metal or metal precursor. Of course, the reverse order of addition is also possible. Exemplary precursors for promoter metals include metal halides, amine solubilized metal hydroxides, metal nitrates or metal oxalates. As indicated above, in the sequential embodiment, each impregnation step preferably is followed by drying and calcination. In the case of promoted bimetallic catalysts as described above, a sequential impregnation may be used, starting with the addition of the promoter metal followed by a second impregnation step involving co-impregnation of the two principal metals, e.g., Pt and Sn.

Hydrogenation of Acetic Acid

The process of hydrogenating acetic acid to form ethyl acetate or a mixture of ethyl acetate and ethanol according to one embodiment of the invention may be conducted in a variety of configurations using a fixed bed reactor or a fluidized bed reactor as one of skill in the art will readily appreciate using catalysts of the first, second or third embodiments. In many embodiments of the present invention, an "adiabatic" reactor can be used; that is, there is little or no need for internal plumbing through the reaction zone to add or remove heat. Alternatively, a shell and tube reactor provided with a heat transfer medium can be used. In many cases, the reaction zone may be housed in a single vessel or in a series of vessels with heat exchangers therebetween. It is considered significant that acetic acid reduction processes using the catalysts of the present invention may be carried out in adiabatic reactors as this reactor configuration is typically far less capital intensive than tube and shell configurations.

Typically, the catalyst is employed in a fixed bed reactor, e.g., in the shape of an elongated pipe or tube where the reactants, typically in the vapor form, are passed over or through the catalyst. Other reactors, such as fluid or ebullient bed reactors, can be employed, if desired. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably the reaction is carried out in the vapor phase under the following conditions. The reaction temperature may the range from of 125° C. to 350° C., e.g., from 200° C. to 325° C., from 225° C. to about 300° C., or from 250° C. to about 300° C. The pressure may range from 10 KPa to 3000 KPa (about 0.1 to 30 atmospheres), e.g., from 50 KPa to 2300 KPa, or from 100 KPa to 1500 KPa. The reactants may be fed to the reactor at a gas hourly space velocities (GHSV) of greater than 500 $hr^{-1}$, e.g., greater than 1000 $hr^{-1}$, greater than 2500 $hr^{-1}$ and even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

In another aspect of the process of this invention, the hydrogenation is carried out at a pressure just sufficient to overcome the pressure drop across the catalytic bed at a suitable GHSV, although there is no bar to the use of higher pressures, it being understood that considerable pressure drop through the reactor bed may be experienced at high space velocities, e.g., on the order of 5000 $hr^{-1}$ or 6,500 $hr^{-1}$.

Although the reaction consumes two moles of hydrogen for every two moles of acetic acid to produce one mole of ethyl acetate, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 4:1, e.g., greater than 5:1 or greater than 10:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

The acetic acid may be vaporized at the reaction temperature, and then the vaporized acetic acid can be fed along with hydrogen in undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid.

In particular, the catalysts and processes of the present invention may achieve favorable conversion of acetic acid and favorable selectivity and productivity to ethyl acetate or mixtures of ethyl acetate and ethanol. For purposes of the present invention, the term conversion refers to the amount of acetic acid in the feed that is convert to a compound other than acetic acid. Conversion is expressed as a mole percentage based on acetic acid in the feed. The conversion of acetic acid (AcOH) is calculated from gas chromatography (GC) data using the following equation:

$$AcOH\ Conv.\ (\%) = 100 * \frac{mmol\ AcOH\ (feed\ stream) - mmol\ AcOH\ (GC)}{mmol\ AcOH\ (feed\ stream)}$$

For purposes of the present invention, the conversion may be at least 10%, e.g., at least 20%, at least 40%, at least 50%, at least 60%, or at least 70% or at least 80%. Although catalysts that have high conversions are desirable, such as at least 80% or at least 90%, a low conversion may be acceptable at high selectivity for ethyl acetate or mixtures of ethyl acetate and ethanol. It is, of course, well understood that in many cases, it is possible to compensate for conversion by appropriate recycle streams or use of larger reactors, but it is more difficult to compensate for poor selectivity.

"Selectivity" is expressed as a mole percent based on converted acetic acid. It should be understood that each compound converted from acetic acid has an independent selectivity and that selectivity is independent from conversion. For example, if 50 mole % of the converted acetic acid is converted to ethyl acetate, we refer to the ethyl acetate selectivity as 50%. Selectivity to ethyl acetate (EtOAc) and mixtures of EtOAc and ethanol (EtOH) is calculated from gas chromatography (GC) data using the following equation:

$$EtOAc\ Sel.\ (\%) = 100 * \frac{mmol\ EtOAc\ (GC)}{\frac{Total\ mmol\ C\ (GC)}{2} - mmol\ AcOH\ (feed\ stream)}$$

wherein "Total mmol C (GC)" refers to total mmols of carbon from all of the products analyzed by gas chromatograph.

For purposes of the present invention, the selectivity to ethoxylates of the catalyst is at least 60%, e.g., at least 70%, or at least 80%. As used herein, "ethoxylates" refers converted compounds that have at least two carbon atoms, such as ethanol, acetaldehyde, ethyl acetate, etc., but excludes ethane. Preferably, the selectivity to ethyl acetate is at least 40%, e.g., at least 50% or at least 60%.

Preferably, the selectivity to mixtures of ethyl acetate and ethanol is at least 50%, e.g., at least 60% or at least 70%. In one embodiment of the present invention, it is preferred that ethyl acetate comprises at a major component of the product mixture, e.g., at least 50 wt %, e.g. from at least 55 wt % or from at least 60 wt %. In addition to ethyl acetate, ethanol also may be formed, for example, at selectivities of at least 20%, e.g. least 30% or at least 40%. In another embodiment of the present invention, the process forms ethanol as a major component, e.g., in an amount greater than 50 wt %, e.g., at least 55 wt % or at least 60 wt %. In this aspect, ethyl acetate may be also be formed, for example, at a selectivities of at least 20%, e.g. at least 30% or at least 40%. It should be understood that in such mixtures, if desired, either the ethyl acetate may be further reacted to form more ethanol, or the ethanol may be further reacted to form more ethyl acetate.

In embodiments of the present invention, it is also desirable to have low selectivity to undesirable products, such as methane, ethane, and carbon dioxide. The selectivity to these undesirable products preferably should be less than 4%, e.g., less than 2% or less than 1%. Preferably, no detectable amounts of these undesirable products are formed during hydrogenation. In several embodiments of the present invention, formation of alkanes is low, usually under 2%, often under 1%, and in many cases under 0.5% of the acetic acid passed over the catalyst is converted to alkanes, which have little value other than as fuel.

Productivity refers to the grams of a specified product, e.g., ethyl acetate, formed during the hydrogenation based on the kilogram of catalyst used per hour. In one embodiment, a productivity of at least 200 grams of ethyl acetate per kilogram catalyst per hour, e.g., at least 400 grams of ethyl acetate or least 600 grams of ethyl acetate, is preferred. In another embodiment, a productivity of at least 200 grams of a mixture of ethyl acetate and ethanol per kilogram catalyst per hour, e.g., at least 400 grams of a mixture of ethyl acetate and ethanol or least 600 grams of ethyl a mixture of ethyl acetate and ethanol, is preferred. In terms of ranges, the productivity preferably to ethyl acetate is from 200 to 3,000 grams of ethyl acetate per kilogram catalyst per hour, e.g., from 400 to 2,500 or from 600 to 2,000.

Some catalysts of the present invention may achieve a conversion of acetic acid of at least 10%, a selectivity to ethyl acetate of at least 60%, and a productivity of at least 200 g of ethyl acetate per kg of catalyst per hour. A subset of catalysts of the invention may achieve a conversion of acetic acid of at least 50%, a selectivity to ethyl acetate of at least 70%, a selectivity to undesirable compounds of less than 4%, and a productivity of at least 600 g of ethyl acetate per kg of catalyst per hour.

Crude Ethyl Acetate Product

In another embodiment, the invention is to a crude ethyl acetate product formed by any of the processes of the present invention. The crude ethyl acetate product produced by the hydrogenation process of the present invention, before any subsequent processing, such as purification and separation, typically will comprise primarily unreacted acetic acid, ethyl acetate and optionally ethanol. In some exemplary embodiments, the crude product comprises ethyl acetate in an amount from 5 wt % to 70 wt. %, e.g., from 15 wt. % to 50 wt. %, or from 20 wt. % to 35 wt. %, based on the total weight of the crude product. The crude product may comprise ethanol in an amount from 5 wt. % to 70 wt. %, e.g., from 15 wt % to 50 wt. %, or from 20 wt. % to 35 wt. %, based on the total weight of the crude product. The crude product typically will further comprise unreacted acetic acid, depending on conversion, for example, in an amount from 5 to 75 wt. %, e.g., from 10 to 60 wt. % or from 20 to 50 wt. %. Since water is formed in the reaction process, water will also be present in the crude product, for example, in amounts ranging from 5 to 50 wt. %, e.g., from 10 to 45 wt. % or from 15 to 35 wt. %. Other components, such as, for example, aldehydes, ketones, alkanes, and carbon dioxide, if detectable, collectively may be present in amounts less than 10 wt. %, e.g., less than 6 or less than 4 wt. %. In terms of ranges other components may be present in an amount from 0.1 to 10 wt. %, e.g., from 0.1 to 6 wt. %, or from 0.1 to 4 wt. %.

In a preferred embodiment, depending on the specific catalyst and process conditions employed, the crude ethyl acetate product may have any of the compositions indicated below in Table 2. Crude mixtures of ethyl acetate and ethanol may have any of the compositions indicated below in Table 3.

TABLE 2

CRUDE ETHYL ACETATE PRODUCT COMPOSITIONS

| Component | Conc. (wt. %) | Conc. (wt. %) | Conc. (wt. %) |
|---|---|---|---|
| Ethyl Acetate | 5-70 | 15-50 | 20-35 |
| Acetic Acid | 5-75 | 10-60 | 20-50 |
| Water | 5-50 | 10-45 | 15-35 |
| Other | <10 | <6 | <4 |

TABLE 3

CRUDE ETHYL ACETATE/ETHANOL MIXTURE PRODUCT COMPOSITIONS

| Component | Conc. (wt. %) | Conc. (wt. %) | Conc. (wt. %) |
|---|---|---|---|
| Ethyl Acetate | 5-70 | 15-50 | 20-35 |
| Ethanol | 5-70 | 15-50 | 20-35 |
| Acetic Acid | 5-75 | 10-60 | 20-50 |
| Water | 5-50 | 10-45 | 15-35 |
| Other | <10 | <6 | <4 |

The raw materials used in connection with the process of this invention may be derived from any suitable source including natural gas, petroleum, coal, biomass and so forth. It is well known to produce acetic acid through methanol carbonylation, acetaldehyde oxidation, ethylene oxidation, oxidative fermentation, and anaerobic fermentation. As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No. 6,232,352 to Vidalin, the disclosure of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syn gas is diverted from the methanol synthesis loop and supplied to a separator unit to recover CO and hydrogen, which are then used to produce acetic acid. In addition to acetic acid, the process can also be used to make hydrogen which may be utilized in connection with this invention.

U.S. Pat. No. RE 35,377 to Steinberg et al., also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syn gas is converted to methanol which may be carbonylated to acetic acid. The method likewise produces hydrogen which may be used in connection with this invention as noted above. See also, U.S. Pat. No. 5,821,111 to Grady et al., which discloses a process for converting waste biomass through gasification into synthesis gas as well as U.S. Pat. No. 6,685,754 to Kindig et al., the disclosures of which are incorporated herein by reference.

Alternatively, acetic acid in vapor form may be taken directly as crude product from the flash vessel of a methanol carbonylation unit of the class described in U.S. Pat. No. 6,657,078 to Scates et al., the entirety of which is incorporated herein by reference. The crude vapor product, for example, may be fed directly to the ethanol synthesis reaction zones of the present invention without the need for condensing the acetic acid and light ends or removing water, saving overall processing costs.

Ethyl acetate obtained by the present invention, may be used in its own right, polymerized, or converted to ethylene through a cracking process. The cracking of ethyl acetate to ethylene is shown below.

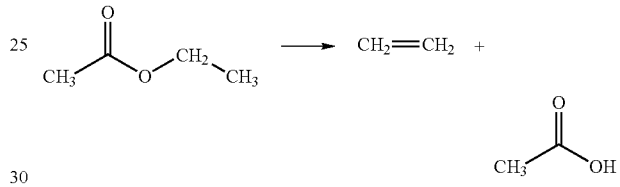

The cracking may be a catalyzed reaction utilizing a cracking catalyst. Suitable cracking catalysts include sulfonic acid resins such as perfluorosulfonic acid resins disclosed in U.S. Pat. No. 4,399,305, noted above, the disclosure of which is incorporated herein by reference. Zeolites are also suitable as cracking catalysts as noted in U.S. Pat. No. 4,620,050, the disclosure of which is also incorporated herein by reference.

Any ethanol in the mixtures of the present invention, may be used in its own right as a fuel or subsequently converted to ethylene which is an important commodity feedstock as it can be converted to polyethylene, vinyl acetate and/or ethyl acetate or any of a wide variety of other chemical products. For example, ethylene can also be converted to numerous polymer and monomer products. The dehydration of ethanol to ethylene is shown below.

Any of known dehydration catalysts can be employed in to dehydrate ethanol, such as those described in copending applications U.S. application Ser. No. 12/221,137 and U.S. application Ser. No. 12/221,138, the entire contents and disclosures of which are hereby incorporated by reference. A zeolite catalyst, for example, may be employed as the dehydration catalyst. While any zeolite having a pore diameter of at least about 0.6 nm can be used, preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated by reference. A zeolite catalyst may be used to concurrently dehydrate ethanol to ethylene and decompose ethyl acetate to ethylene in a highly efficient process of the invention.

In embodiments where a mixture of ethyl acetate and ethanol is formed, it may be desired to further react the mixture in order to enrich the mixture in either the ethyl acetate or ethanol. For example, if desired, the ethanol concentration in the mixture may be increased through hydrolysis of the ethyl acetate in the presence of an acid catalyst to make additional ethanol and acetic acid. The acetic acid then may be recycled back in the hydrogenation process.

The following examples describe the procedures used for the preparation of various catalysts employed in the process of this invention.

EXAMPLES

Catalyst Preparations (General)

The catalyst supports were dried at 120° C. overnight under circulating air prior to use. All commercial supports (i.e., $SiO_2$, $TiO_2$) were used as a 14/30 mesh, or in its original shape (1/16 inch or 1/8 inch pellets) unless mentioned otherwise. Powdered materials were pelletized, crushed and sieved after the metals had been added. The individual catalyst preparations of the invention, as well as comparative examples, are described in detail below.

Example 1

$SiO_2$—$CaSiO_3$(5)-Pt(3)-Sn(1.8)

The catalyst was prepared by first adding $CaSiO_3$ (Aldrich) to the $SiO_2$ catalyst support, followed by the addition of Pt/Sn. First, an aqueous suspension of $CaSiO_3$ 200 mesh) was prepared by adding 0.52 g of the solid to 13 ml of deionized $H_2O$, followed by the addition of 1.0 ml of colloidal $SiO_2$ (15 wt % solution, NALCO). The suspension was stirred for 2 h at room temperature and then added to 10.0 g of $SiO_2$ catalyst support (14/30 mesh) using incipient wetness technique. After standing for 2 hours, the material was evaporated to dryness, followed by drying at 120° C. overnight under circulating air and calcination at 500° C. for 6 hours. All of the $SiO_2$—$CaSiO_3$ material was then used for Pt/Sn metal impregnation.

The catalysts were prepared by first adding $Sn(OAc)_2$ (tin acetate, $Sn(OAc)_2$ from Aldrich) (0.4104 g, 1.73 mmol) to a vial containing 6.75 ml of 1:1 diluted glacial acetic acid (Fisher). The mixture was stirred for 15 min at room temperature, and then, 0.6711 g (1.73 mmol) of solid $Pt(NH_3)_4(NO_3)_2$ (Aldrich) were added. The mixture was stirred for another 15 min at room temperature, and then added drop wise to 5.0 g of $SiO_2$—$CaSiO_3$ support, in a 100 ml round-bottomed flask. The metal solution was stirred continuously until all of the Pt/Sn mixture had been added to the $SiO_2$—$CaSiO_3$ support while rotating the flask after every addition of metal solution. After completing the addition of the metal solution, the flask containing the impregnated catalyst was left standing at room temperature for two hours. The flask was then attached to a rotor evaporator (bath temperature 80° C.), and evacuated until dried while slowly rotating the flask. The material was then dried further overnight at 120° C., and then calcined using the following temperature program: 25°→160° C./ramp 5.0 deg/min; hold for 2.0 hours; 160→500° C./ramp 2.0 deg/min; hold for 4 hours. Yield: 11.21 g of dark grey material.

Example 2

$KA160$-$CaSiO_3$(8)-Pt(3)-Sn(1.8)

The material was prepared by first adding $CaSiO_3$ to the KA160 catalyst support ($SiO_2$-(0.05) $Al_2O_3$, Sud Chemie, 14/30 mesh), followed by the addition of Pt/Sn. First, an aqueous suspension of $CaSiO_3$(≤200 mesh) was prepared by adding 0.42 g of the solid to 3.85 ml of deionized $H_2O$, followed by the addition of 0.8 ml of colloidal $SiO_2$ (15 wt % solution, NALCO). The suspension was stirred for 2 h at room temperature and then added to 5.0 g of KA160 catalyst support (14/30 mesh) using incipient wetness technique. After standing for 2 hours, the material was evaporated to dryness, followed by drying at 120° C. overnight under circulating air and calcinations at 500° C. for 6 hours. All of the KA160-$CaSiO_3$ material was then used for Pt/Sn metal impregnation.

The catalysts were prepared by first adding $Sn(OAc)_2$ (tin acetate, $Sn(OAc)_2$ from Aldrich) (0.2040 g, 0.86 mmol) to a vial containing 6.75 ml of 1:1 diluted glacial acetic acid (Fisher). The mixture was stirred for 15 min at room temperature, and then, 0.3350 g (0.86 mmol) of solid $Pt(NH_3)_4(NO_3)_2$ (Aldrich) were added. The mixture was stirred for another 15 min at room temperature, and then added drop wise to 5.0 g of $SiO_2$—$CaSiO_3$ support, in a 100 ml round-bottomed flask. After completing the addition of the metal solution, the flask containing the impregnated catalyst was left standing at room temperature for two hours. The flask was then attached to a rotor evaporator (bath temperature 80° C.), and evacuated until dried while slowly rotating the flask. The material was then dried further overnight at 120° C., and then calcined using the following temperature program: 25°→160° C./ramp 5.0 deg/min; hold for 2.0 hours; 160→500° C./ramp 2.0 deg/min; hold for 4 hours. Yield: 5.19 g of tan-colored material.

Example 3

$SiO_2$—$CaSiO_3$(2.5)-Pt(1.5)-Sn(0.9)

This catalyst was prepared in the same manner as Example 1, with the following starting materials: 0.26 g of $CaSiO_3$ as a support modifier; 0.5 ml of colloidal $SiO_2$ (15 wt % solution, NALCO), 0.3355 g (0.86 mmol) of $Pt(NH_3)_4(NO_3)_2$; and 0.2052 g (0.86 mmol) of $Sn(OAc)_2$. Yield: 10.90 g of dark grey material.

Example 4

$SiO_2$+$MgSiO_3$—Pt(1.0)-Sn(1.0)

This catalyst was prepared in the same manner as Example 1, with the following starting materials: 0.69 g of Mg(AcO) as a support modifier; 1.3 g of colloidal $SiO_2$ (15 wt. % solution, NALCO), 0.2680 g (0.86 mmol) of $Pt(NH_3)_4(NO_3)_2$; and 0.1640 g (0.86 mmol) of $Sn(OAc)_2$. Yield: 8.35 g. The $SiO_2$ support is impregnated with a solution of Mg(AcO) and colloidal $SiO_2$. The support is dried and then calcined to 700° C.

Example 5

$SiO_2$—$CaSiO_3$(5)-Re(4.5)-Pd(1)

The $SiO_2$—$CaSiO_3$(5) modified catalyst support was prepared as described in Example 1. The Re/Pd catalyst was prepared then by impregnating the $SiO_2$—$CaSiO_3$(5) (1/16 inch extrudates) with an aqueous solution containing $NH_4ReO_4$ and $Pd(NO_3)_2$. The metal solutions were prepared by first adding $NH_4ReO_4$ (0.7237 g, 2.70 mmol) to a vial containing 12.0 ml of deionized $H_2O$. The mixture was stirred for 15 min at room temperature, and 0.1756 g (0.76 mmol) of solid $Pd(NO_3)_2$ was then added. The mixture was stirred for another 15 min at room temperature, and then added drop wise to 10.0 g of dry $SiO_2$-(0.05)$CaSiO_3$ catalyst support in a 100 ml round-bottomed flask. After completing the addition of the metal solution, the flask containing the impregnated catalyst was left standing at room temperature for two hours. All other manipulations (drying, calcination) were carried out as described in Example 1. Yield: 10.9 g of brown material.

Example 6

$SiO_2$—ZnO(5)-Pt(1)-Sn(1)

Powdered and meshed high surface area silica NPSG SS61138 (100 g) of uniform particle size distribution of about 0.2 mm was dried at 120° C. in a circulating air oven atmosphere overnight and then cooled to room temperature. To this was added a solution of zinc nitrate hexahydrate. The resulting slurry was dried in an oven gradually heated to 110° C. (>2 hours, 10° C./min.) then calcined. To this was added a solution of platinum nitrate (Chempur) in distilled water and a solution of tin oxalate (Alfa Aesar) (1.74 g) in dilute nitric acid (1N, 8.5 ml) The resulting slurry was dried in an oven gradually heated to 110° C. (>2 hours, 10° C./min.). The impregnated catalyst mixture was then calcined at 500° C. (6 hours, 1° C./min).

Example 7

$TiO_2$—$CaSiO_3$(5)-Pt(3)-Sn(1.8)

The material was prepared by first adding $CaSiO_3$ to the $TiO_2$ catalyst (Anatase, 14/30 mesh) support, followed by the addition of Pt/Sn as described in Example 1. First, an aqueous suspension of $CaSiO_3$ 200 mesh) was prepared by adding 0.52 g of the solid to 7.0 ml of deionized $H_2O$, followed by the addition of 1.0 ml of colloidal $SiO_2$ (15 wt % solution, NALCO). The suspension was stirred for 2 h at room temperature and then added to 10.0 g of $TiO_2$ catalyst support (14/30 mesh) using incipient wetness technique. After standing for 2 hours, the material was evaporated to dryness, followed by drying at 120° C. overnight under circulating air and calcination at 500° C. for 6 hours. All of the $TiO_2$—$CaSiO_3$ material was then used for Pt/Sn metal impregnation using 0.6711 g (1.73 mmol) of $Pt(NH_3)_4(NO_3)_2$ and 0.4104 g (1.73 mmol) of $Sn(OAc)_2$ following the procedure described in Example 1. Yield: 11.5 g of light grey material.

Example 8

Pt(2)-Sn(2) on High Surface Area Silica

Powdered and meshed high surface area silica NPSG SS61138 (100 g) of uniform particle size distribution of about 0.2 mm was dried at 120° C. in a circulating air oven atmosphere overnight and then cooled to room temperature. To this was added a solution of nitrate hexahydrate (Chempur). The resulting slurry was dried in an oven gradually heated to 110° C. (>2 hours, 10° C./min.) then calcined. To this was added a solution of platinum nitrate (Chempur) in distilled water and a solution of tin oxalate (Alfa Aesar) in dilute nitric acid. The resulting slurry was dried in an oven gradually heated to 110° C. (>2 hours, 10° C./min.). The impregnated catalyst mixture was then calcined at 500° C. (6 hours, 1° C./min).

Example 9

KA160-Pt(3)-Sn(1.8)

The material was prepared by incipient wetness impregnation of KA160 catalyst support ($SiO_2$-(0.05) $Al_2O_3$, Sud Chemie, 14/30 mesh) as described in Example 1. The metal solutions were prepared by first adding $Sn(OAc)_2$ (0.2040 g, 0.86 mmol) to a vial containing 4.75 ml, of 1:1 diluted glacial acetic acid. The mixture was stirred for 15 min at room temperature, and then, 0.3350 g (0.86 mmol) of solid $Pt(NH_3)_4(NO_3)_2$ were added. The mixture was stirred for another 15 min at room temperature, and then added drop wise to 5.0 g of dry KA160 catalyst support (14/30 mesh) in a 100 ml round-bottomed flask. All other manipulations, drying and calcination was carried out as described in Example 16. Yield: 5.23 g of tan-colored material.

Example 10

$SiO_2$-$SnO_2$(5)-Pt(1)-Zn(1)

Powdered and meshed high surface area silica NPSG SS61138 (100 g) of uniform particle size distribution of about 0.2 mm was dried at 120° C. in a circulating air oven atmosphere overnight and then cooled to room temperature. To this was added a solution of tin acetate ($Sn(OAc)_2$). The resulting slurry was dried in an oven gradually heated to 110° C. (>2 hours, 10° C./min.) then calcined. To this was added a solution of platinum nitrate (Chempur) in distilled water and a solution of tin oxalate (Alfa Aesar) in dilute nitric acid The resulting slurry was dried in an oven gradually heated to 110° C. (>2 hours, 10° C./min.). The impregnated catalyst mixture was then calcined at 500° C. (6 hours, 1° C./min).

Example 11

$SiO_2$—$TiO_2$(10)-Pt(3)-Sn(1.8)

The $TiO_2$-modified silica support was prepared as follows. A solution of 4.15 g (14.6 mmol) of $Ti\{OCH(CH_3)_2\}_4$ in 2-propanol (14 ml) was added dropwise to 10.0 g of $SiO_2$ catalyst support (1/16 inch extrudates) in a 100 ml round-bottomed flask. The flask was left standing for two hours at room temperature, and then evacuated to dryness using a rotor evaporator (bath temperature 80° C.). Next, 20 ml of deionized $H_2O$ was slowly added to the flask, and the material was left standing for 15 min. The resulting water/2-propanol was then removed by filtration, and the addition of $H_2O$ was repeated two more times. The final material was dried at 120° C. overnight under circulation air, followed by calcination at 500° C. for 6 hours. All of the $SiO_2$—$TiO_2$ material was then used for Pt/Sn metal impregnation using 0.6711 g (1.73 mmol) of $Pt(NH_3)_4(NO_3)_2$ and 0.4104 g (1.73 mmol) of $Sn(OAc)_2$ following the procedure described above for Example 1. Yield: 11.98 g of dark grey 1/16 inch extrudates.

Example 12

$SiO_2$—$WO_3$(10)-Pt(3)-Sn(1.8)

The $WO_3$-modified silica support was prepared as follows. A solution of 1.24 g (0.42 mmol) of $(NH_4)_6H_2W_{12}O_{40}$.n $H_2O$, (AMT) in deionized $H_2O$ (14 ml) was added dropwise to 10.0 g of $SiO_2$ NPSGSS 61138 catalyst support (SA=250 m²/g, 1/16 inch extrudates) in a 100 ml round-bottomed flask. The flask was left standing for two hours at room temperature, and then evacuated to dryness using a rotor evaporator (bath temperature 80° C.). The resulting material was dried at 120° C. overnight under circulation air, followed by calcination at 500° C. for 6 hours. All of the (light yellow) $SiO_2$—$WO_3$ material was then used for Pt/Sn metal impregnation using 0.6711 g (1.73 mmol) of $Pt(NH_3)_4(NO_3)_2$ and 0.4104 g (1.73 mmol) of Sn(OAc)$_2$ following the procedure described above for Example 1. Yield: 12.10 g of dark grey 1/16 inch extrudates.

Example 13

Comparative

Sn(0.5) on High Purity Low Surface Area Silica. Powdered and meshed high purity low surface area silica (100 g) of uniform particle size distribution of about 0.2 mm was dried at 120° C. in an oven under nitrogen atmosphere overnight and then cooled to room temperature. To this was added a solution of tin oxalate (Alfa Aesar) (1.74 g) in dilute nitric acid (1N, 8.5 ml). The resulting slurry was dried in an oven gradually heated to 110° C. (>2 hours, 10° C./min.). The impregnated catalyst mixture was then calcined at 500° C. (6 hours, 1° C./min).

Example 14

Gas Chromatographic (GC) Analysis of the Crude Product Hydrogenation

Catalyst of Examples 1-13 were tested to determine the selectivity and productivity to ethyl acetate and ethanol as shown in Table 4.

In a tubular reactor made of stainless steel, having an internal diameter of 30 mm and capable of being raised to a controlled temperature, there are arranged 50 ml of catalyst listed in Table 2. The length of the combined catalyst bed after charging was approximately about 70 mm. The reaction feed liquid of acetic acid was evaporated and charged to the reactor along with hydrogen and helium as a carrier gas with an average combined gas hourly space velocity (GHSV), temperature, and pressure as indicated in Table 4. The feed stream contained a mole ratio hydrogen to acetic acid as indicated in Table 4.

The analysis of the products was carried out by online GC. A three channel compact GC equipped with one flame ionization detector (FID) and 2 thermal conducting detectors (TCDs) was used to analyze the reactants and products. The front channel was equipped with an FID and a CP-Sil 5 (20 m)+WaxFFap (5 m) column and was used to quantify: Acetaldehyde; Ethanol; Acetone; Methyl acetate; Vinyl acetate; Ethyl acetate; Acetic acid; Ethylene glycol diacetate; Ethylene glycol; Ethylidene diacetate; and Paraldehyde. The middle channel was equipped with a TCD and Porabond Q column and was used to quantify: CO$_2$; ethylene; and ethane. The back channel was equipped with a TCD and Molsieve 5A column and was used to quantify: Helium; Hydrogen; Nitrogen; Methane; and Carbon monoxide.

Prior to reactions, the retention time of the different components was determined by spiking with individual compounds and the GCs were calibrated either with a calibration gas of known composition or with liquid solutions of known compositions. This allowed the determination of the response factors for the various components.

TABLE 4

| | | Reaction Conditions | | | | | Selectivity (%) | |
|---|---|---|---|---|---|---|---|---|
| Cat. Ex. | Cat. | Ratio of H$_2$:AcOH | Press. (KPa) | Temp. (° C.) | GHSV (hr$^{-1}$) | Conv. of AcOH (%) | EtOAc | EtOH |
| 1 | SiO$_2$—CaSiO$_3$(5)-Pt(3)-Sn(1.8) | 5:1 | 2200 | 250 | 2500 | 24 | 6 | 92 |
| 2 | KA160-CaSiO$_3$(8)-Pt(3)-Sn(1.8) | 5:1 | 2200 | 250 | 2500 | 43 | 13 | 84 |
| 3 | SiO$_2$—CaSiO$_3$(2.5)-Pt(1.5)-Sn(0.9) | 10:1 | 1400 | 250 | 2500 | 26 | 8 | 86 |
| 4 | SiO$_2$ + MgSiO$_3$—Pt(1.0)-Sn(1.0) | 4:1 | 1400 | 250 | 6570 | 22 | 10 | 88 |
| 5 | SiO$_2$—CaSiO$_3$(5)-Re(4.5)-Pd(1) | 5:1 | 1400 | 250 | 6570 | 8 | 17 | 83 |
| 6 | SiO$_2$—ZnO(5)-Pt(1)-Sn(1) | 4:1 | 1400 | 275 | 6570 | 22 | 21 | 76 |
| 7 | TiO$_2$—CaSiO$_3$(5)-Pt(3)-Sn(1.8) | 5:1 | 1400 | 250 | 6570 | 38 | 78 | 22 |
| 8 | Pt(2)-Sn(2) on SiO$_2$ | 5:1 | 1400 | 296 | 6570 | 34 | 64 | 33 |
| 8 | Pt(2)-Sn(2) on SiO$_2$ | 5:1 | 1400 | 280 | 6570 | 37 | 62 | 36 |
| 8 | Pt(2)-Sn(2) on SiO$_2$ | 5:1 | 1400 | 250 | 6570 | 26 | 63 | 36 |
| 8 | Pt(2)-Sn(2) on SiO$_2$ | 5:1 | 1400 | 225 | 6570 | 11 | 57 | 42 |
| 9 | KA160-Pt(3)-Sn(1.8) | 5:1 | 2200 | 250 | 2500 | 61 | 50 | 47 |
| 10 | SiO$_2$—SnO$_2$(5)-Pt(1)-Zn(1) | 4:1 | 1400 | 275 | 6570 | 13 | 44 | 48 |
| 11 | SiO$_2$—TiO$_2$(10)-Pt(3)-Sn(1.8) | 5:1 | 1400 | 250 | 6570 | 73 | 53 | 47 |
| 12 | SiO$_2$—WO$_3$(10)-Pt(3)-Sn(1.8) | 5:1 | 1400 | 250 | 6570 | 17 | 23 | 77 |
| 13 | Sn(0.5) on SiO$_2$ | 9:1~8:1 | 2200 | 250 | 2500 | 10 | — | 1 |

Example 15

Figure 4:
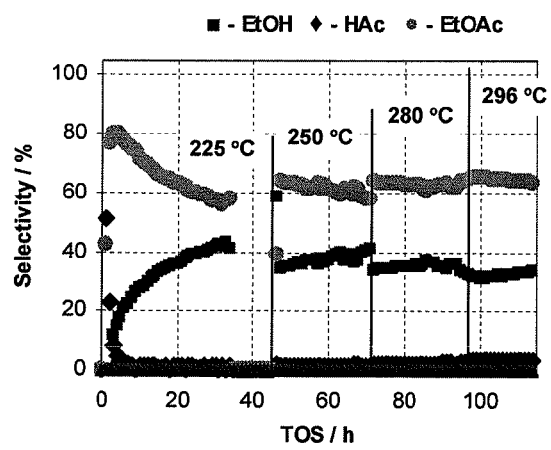
FIG. 4 is a graph of the activity of a catalyst compared to the selectivity of the catalyst to a mixture of ethyl acetate and ethanol at various temperatures according to one embodiment of the invention.

Vaporized acetic acid and hydrogen were passed over a hydrogenation catalyst of the present invention comprising 2 wt % Pt; and 2 wt % Sn on high surface area silica (NPSG SS61138) having a surface area of approximately 250 m$^2$/g at a ratio of hydrogen to acetic acid of about 160 sccm/min H$_2$: 0.09 g/min HOAc, the hydrogen being diluted with about 60 sccm/min N$_2$ at a space velocity of about 6570 hr$^{-1}$ and a pressure of 200 psig (1379 kPag). The temperature was increased at about 50 hrs, 70 hrs and 90 hrs as indicated in FIG. 3 and FIG. 4. The productivity in grams of the indicated products (ethanol, acetaldehyde, and ethyl acetate) per kilogram of catalyst per hour are indicated in FIG. 3, and the selectivity of a catalyst for the various products are indicated in FIG. 4 with the upper line indicating productivity of or selectivity to ethyl acetate, the intermediate line indicating ethanol and the lower line indicating acetaldehyde. It is considered especially significant that production of, and selectivity for, acetaldehyde were low. FIGS. 3 and 4 demonstrate that the relative insensitivity of the catalyst to changes in temperature make this catalyst well-suited for use in a so-called adiabatic reactor in which the temperature may vary substantially over the catalyst bed due to the low and uneven rate of heat removal from the reactor.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethyl acetate, comprising hydrogenating acetic acid in the presence of a catalyst under conditions effective to form ethyl acetate, wherein the catalyst comprises a first metal, a second metal and a support, wherein the first metal is selected from the group consisting of nickel, palladium and platinum and is present in an amount greater than 1 wt %, based on the total weight of the catalyst, and a second metal selected from the group consisting of copper, cobalt, tin and zinc.

2. The process of claim 1, wherein the first metal is present in an amount greater than 1 wt. % and less than 25 wt % , based on the total weight of the catalyst.

3. The process of claim 1, wherein the support is present in an amount of 25 wt. % to 99 wt. %, based on the total weight of the catalyst.

4. The process of claim 1, wherein the support is selected from the group consisting of iron oxide, silica, alumina, silica/aluminas, titania, zirconia, magnesium oxide, calcium silicate, carbon, graphite, high surface area graphitized carbon, activated carbons, and mixtures thereof.

5. The process of claim 1, further comprising at least one support modifier selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof.

6. The process of claim 1, further comprising at least one support modifier selected from the group consisting of oxides of Group IVB metals, oxides of Group VB metals, oxides of Group VIB metals, iron oxides, aluminum oxides and mixtures thereof.

7. The process of claim 1, wherein the second metal is present in an amount of from 0.1 to 10 wt. %, based on the total weight of the catalyst.

8. The process of claim 1, wherein at least 10% of the acetic acid is converted during hydrogenation.

9. The process of claim 1, wherein the hydrogenation has a selectivity to ethyl acetate of at least 40%.

10. The process of claim 1, wherein the hydrogenation has a selectivity to methane, ethane, and carbon dioxide of less than 4%.

11. The process of claim 1, wherein the catalyst has a surface area of from 50 $m^2/g$ to 600 $m^2/g$.

12. The process of claim 1, wherein the acetic acid is obtained from a coal source, natural gas source or biomass source.

13. The process of claim 1, further comprising cracking the ethyl acetate obtained during the hydrogenation to produce ethylene.

14. The process of claim 1, wherein the hydrogenation is performed in a vapor phase at a temperature of from 125° C. to 350° C., a pressure of 10 KPa to 3000 KPa, and a hydrogen to acetic acid mole ratio of greater than 4:1.

15. The process of claim 1, further comprising producing ethanol in addition to the ethyl acetate, wherein the selectivity to ethanol is at least 20%.

16. The process of claim 1, further comprising continuously withdrawing a crude product formed by the hydrogenating acetic acid, wherein the crude ethanol product comprises:
  (a) ethyl acetate in an amount from 15 to 50 wt. %;
  (b) ethanol in an amount from 5 to 70 wt. %;
  (c) acetic acid in an amount from 10 to 60 wt. %;
  (d) water in an amount from 10 to 45 wt. %; and
  (e) any other compounds in an amount less than 6 wt. %, wherein all weight percents are based on the total weight of the crude product.

17. A process for producing ethyl acetate, comprising hydrogenating acetic acid in the presence of a catalyst under conditions effective to form ethyl acetate, wherein the catalyst comprises a first metal, a second metal and a support, wherein the first metal is selected from group consisting of nickel and palladium and is present in an amount from 0.1 to 25 wt. %, based on the total weight of the catalyst, wherein the second metal is selected from the group consisting of tin and zinc.

18. The process of claim 17, wherein the support is present in an amount from 25 wt % to 99.9 wt %, based on the total weight of the catalyst.

19. The process of claim 17, wherein the support has a surface area of from 50 $m^2/g$ to 600 $m^2/g$.

20. The process of claim 17, wherein the support is selected from the group consisting of iron oxide, silica, alumina, silica/aluminas, titania, zirconia, magnesium oxide, calcium silicate, carbon, graphite, high surface area graphitized carbon, activated carbons, and mixtures thereof.

21. The process of claim 17, further comprising at least one support modifier selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof.

22. The process of claim 17, further comprising at least one support modifier selected from the group of oxides of Group IVB metals, oxides of Group VB metals, oxides of Group VIB metals, iron oxides, aluminum oxides and mixtures thereof.

23. The process of claim 17, wherein the second metal is present in an amount of from 0.1 to 10 wt. %, based on the total weight of the catalyst.

24. The process of claim 17, wherein at least 10% of the acetic acid is converted during hydrogenation.

25. The process of claim 17, wherein the hydrogenation has a selectivity to ethyl acetate of at least 40%.

26. The process of claim 17, wherein the hydrogenation has a selectivity to methane, ethane, and carbon dioxide and mixtures thereof of less than 4%.

27. The process of claim 17, wherein the acetic acid is obtained from a coal source, natural gas source or biomass source.

28. The process of claim 17, further comprising dehydrating the ethyl acetate obtained during the hydrogenation to produce ethylene.

29. The process of claim 17, wherein the hydrogenation is performed in a vapor phase at a temperature of from 125° C. to 350° C., a pressure of 10 KPa to 3000 KPa, and a hydrogen to acetic acid mole ratio of greater than 4:1.

30. The process of claim 17, further comprising producing ethanol in addition to the ethyl acetate, wherein the selectivity to ethanol is at least 20%.

31. A process for producing ethyl acetate comprising hydrogenating acetic acid in the presence of a catalyst under conditions effective to form ethyl acetate, wherein the catalyst comprises a first metal selected from the group consisting of cobalt, nickel, ruthenium, rhodium, palladium, osmium, iridium, platinum, titanium, zinc, chromium, a second metal selected from the group consisting of copper, tin, chromium, iron, vanadium, lanthanum, cerium, manganese, and nickel, wherein the second metal is different than the first metal, a support, and at least one support modifier selected from the group of oxides of Group IVB metals, oxides of Group VB metals, oxides of Group VIB metals, iron oxides, aluminum oxides and mixtures thereof.

32. The process of claim 31, wherein the first metal is present in an amount of from 0.1 to 25 wt. %, based on the total weight of the catalyst.

33. The process of claim 31, wherein the at least one support modifier is selected from the group consisting of $WO_3$, $MoO_3$, $Fe_2O_3$, $Cr_2O_3$, $TiO_2$, $ZrO_2$, $Nb_2O_5$, $Ta_2O_5$, and $Al_2O_3$.

34. The process of claim 31, wherein the at least one support modifier is present in an amount of 0.1 wt. % to 50 wt. %, based on the total weight of the catalyst.

35. The process of claim 31, wherein the support is present in an amount of 25 wt. % to 99 wt. %, based on the total weight of the catalyst.

36. The process of claim 31, wherein the support is selected from the group consisting of iron oxide, silica, alumina, silica/aluminas, titania, zirconia, magnesium oxide, calcium silicate, carbon, graphite, high surface area graphitized carbon, activated carbons, and mixtures thereof.

37. The process of claim 31, wherein the first metal is platinum and the second metal is tin.

38. The process of claim 31, wherein the second metal is present in an amount of from 0.1 to 10 wt. %, based on the total weight of the catalyst.

39. The process of claim 31, wherein the catalyst further comprises a third metal different from the first and second metals.

40. The process of claim 39, wherein the third metal is selected from the group consisting of cobalt, palladium, ruthenium, copper, zinc, platinum, and tin.

41. The process of claim 39, wherein the third metal is present in an amount of 0.05 and 4 wt. %, based on the total weight of the catalyst.

42. The process of claim 31, wherein at least 10% of the acetic acid is converted during hydrogenation.

43. The process of claim 31, wherein the hydrogenation has a selectivity to ethyl acetate of at least 40%.

44. The process of claim 31, wherein the hydrogenation has a selectivity to methane, ethane, and carbon dioxide and mixtures thereof of less than 4%.

45. The process of claim 31, wherein the acetic acid is obtained from a coal source, natural gas source or biomass source.

46. The process of claim 31, further comprising dehydrating the ethyl acetate obtained during the hydrogenation to ethylene.

47. The process of claim 31, wherein the hydrogenation is performed in a vapor phase at a temperature of from 125° C. to 350° C., a pressure of 10 KPa to 3000 KPa, and a hydrogen to acetic acid mole ratio of greater than 4:1.

48. The process of claim 31, further comprising producing ethanol in addition to the ethyl acetate, wherein the selectivity to ethanol is at least 20%.

49. The process of claim 31, wherein the process forms a crude ethyl acetate product having the following composition:
(a) ethyl acetate in an amount from 5 to 70 wt. %;
(b) acetic acid in an amount from 5 to 75 wt. %;
(c) water in an amount from 5 to 50 wt. %; and
(d) any other compounds in an amount less than 10 wt. %, wherein all weight percents are based on the total weight of the crude product.

50. The process of claim 1, wherein the catalyst has a productivity that decreases less than 6% per 100 hours of catalyst usage.

51. The process of claim 17, wherein the catalyst has a productivity that decreases less than 6% per 100 hours of catalyst usage.

52. The process of claim 31, wherein the catalyst has a productivity that decreases less than 6% per 100 hours of catalyst usage.

* * * * *